United States Patent
McNamara

(10) Patent No.: US 12,378,591 B2
(45) Date of Patent: Aug. 5, 2025

(54) DIGITAL NUCLEASE DETECTION COMPOSITIONS AND METHODS

(71) Applicant: UNIVERSITY OF IOWA RESEARCH FOUNDATION, Iowa City, IA (US)

(72) Inventor: James O. McNamara, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 1257 days.

(21) Appl. No.: 16/651,863

(22) PCT Filed: Sep. 27, 2018

(86) PCT No.: PCT/US2018/053107
§ 371 (c)(1),
(2) Date: Mar. 27, 2020

(87) PCT Pub. No.: WO2019/067711
PCT Pub. Date: Apr. 4, 2019

(65) Prior Publication Data
US 2020/0255883 A1 Aug. 13, 2020

Related U.S. Application Data

(60) Provisional application No. 62/565,674, filed on Sep. 29, 2017.

(51) Int. Cl.
*C12Q 1/68* (2018.01)
*C12Q 1/6813* (2018.01)
*C12Q 1/6883* (2018.01)

(52) U.S. Cl.
CPC ............. *C12Q 1/68* (2013.01); *C12Q 1/6813* (2013.01); *C12Q 1/6883* (2013.01); *C12Q 2521/301* (2013.01); *C12Q 2521/319* (2013.01)

(58) Field of Classification Search
None
See application file for complete search history.

(56) References Cited

U.S. PATENT DOCUMENTS

| | | |
|---|---|---|
| 3,770,631 A | 11/1973 | Fekete et al. |
| 5,538,848 A | 7/1996 | Livak et al. |
| 5,837,547 A | 11/1998 | Schwartz |
| 5,910,584 A | 6/1999 | Yamamoto |
| 6,773,885 B1 | 8/2004 | Walder et al. |
| 7,041,807 B1 | 5/2006 | Cashman et al. |
| 7,439,341 B2 | 10/2008 | Laikhter et al. |
| 7,803,536 B2 | 9/2010 | Behlke et al. |
| 8,871,444 B2 | 10/2014 | Griffiths et al. |
| 9,603,949 B2 | 3/2017 | McNamara |
| 10,619,219 B2 | 4/2020 | McNamara et al. |
| 10,635,800 B2 | 4/2020 | Bakish |
| 2003/0092175 A1 | 5/2003 | Kato |
| 2004/0137479 A1 | 7/2004 | Walder et al. |
| 2005/0026284 A1 | 2/2005 | Kudlicki et al. |
| 2006/0003952 A1 | 1/2006 | Ravikumar et al. |
| 2006/0014187 A1 | 1/2006 | Li et al. |
| 2006/0024765 A1 | 2/2006 | Horii et al. |
| 2006/0036087 A1 | 2/2006 | Eckstein |
| 2006/0088833 A1 | 4/2006 | Bange et al. |
| 2006/0105360 A1 | 5/2006 | Croce |

(Continued)

FOREIGN PATENT DOCUMENTS

| | | |
|---|---|---|
| CN | 102131915 A | 7/2011 |
| EP | 2669663 A1 | 12/2013 |

(Continued)

OTHER PUBLICATIONS

Colin et al Nature Communications. Dec. 7, 2015. 6:10008, p. 1-12 (Year: 2015).*
Taly et al Jul. 2012. Trends in Molecular Medicine. 18(7): 405-416 (Year: 2012).*
Iwobi, A , et al., "Droplet digital PCR for routine analysis of genetically modified foods (GMO) e A comparison with real-time quantitative PCR", Food Control 69, 205-213 (2016).
Lee, A , et al., "Single-Molecule Enzymology of Chymotrypsin Using Water-in-Oil Emulsion", Biophys J 88 (6), 4303-4311 (2005).

(Continued)

*Primary Examiner* — Carla J Myers
(74) *Attorney, Agent, or Firm* — Viksnins Harris Padys Malen LLP

(57) ABSTRACT

In certain embodiments, the present invention provides a detection composition comprising a picodroplet comprising (a) an aqueous solution, and (b) a substrate probe comprising (i) an oligonucleotide of 2 to 75 nucleotides in length, (ii) a fluorophore operably linked to the oligonucleotide, and (iii) a quencher operably linked to the oligonucleotide. As used herein, the term "picodroplet" comprises a liquid droplet that has a volume of 0.014 to 2.6 picoliters. In certain embodiments, the present invention provides a method of detecting at least one individual nuclease molecule present in a sample, comprising contacting an aqueous sample suspected of containing at least one nuclease with at least one detection composition comprising a picodroplet comprising (a) an aqueous solution, and (b) a substrate probe comprising (i) an oligonucleotide of 2 to 75 nucleotides in length, (ii) a fluorophore operably linked to the oligonucleotide, and (iii) a quencher operably linked to the oligonucleotide to form an aqueous reaction mixture; emulsifying the aqueous mixture in oil to form picoliter-scale droplets in an emulsion, (c) incubating the picoliter-scale droplets in the emulsion in order for the nuclease, if present, to digest the substrate probes linked to the microbeads; recovering the microbeads; and detecting fluorescence emitting from the microbeads.

19 Claims, 11 Drawing Sheets

Specification includes a Sequence Listing.

(56) References Cited

U.S. PATENT DOCUMENTS

| | | | |
|---|---|---|---|
| 2006/0270624 | A1 | 11/2006 | Cook et al. |
| 2007/0105123 | A1 | 5/2007 | Patterson |
| 2007/0238957 | A1 | 10/2007 | Yared |
| 2009/0325169 | A1 | 12/2009 | Walder et al. |
| 2010/0041086 | A1 | 2/2010 | Pamula et al. |
| 2010/0221717 | A1 | 9/2010 | Chen et al. |
| 2010/0298554 | A1 | 11/2010 | Laikhter et al. |
| 2010/0323348 | A1 | 12/2010 | Hamady et al. |
| 2011/0003290 | A1 | 1/2011 | Gale et al. |
| 2012/0028251 | A1 | 2/2012 | Mach |
| 2012/0329160 | A1 | 12/2012 | Hong et al. |
| 2015/0037805 | A1 | 2/2015 | Zhang |
| 2016/0282269 | A1 | 9/2016 | Schmidt et al. |
| 2017/0225167 | A1 | 8/2017 | Boehm et al. |

FOREIGN PATENT DOCUMENTS

| | | | |
|---|---|---|---|
| WO | 1995031481 | A1 | 11/1995 |
| WO | 2001021830 | A1 | 3/2001 |
| WO | 2010150103 | A2 | 12/2010 |
| WO | 2011020011 | A2 | 2/2011 |
| WO | 2011063388 | A2 | 5/2011 |
| WO | 2011020011 | A3 | 6/2011 |
| WO | 2011133433 | A2 | 10/2011 |
| WO | 2013033436 | A1 | 3/2013 |
| WO | 2013048583 | A2 | 4/2013 |
| WO | 2014143228 | A1 | 9/2014 |
| WO | 2015120406 | A1 | 8/2015 |
| WO | 2018167666 | A1 | 9/2018 |
| WO | 2019070612 | A1 | 4/2019 |
| WO | 2020111713 | A1 | 6/2020 |

OTHER PUBLICATIONS

Obayashi, Y, et al., "A single-molecule digital enzyme assay using alkaline phosphatase with a cumarin-based fluorogenic substrate", Analyst 140 (15), 5065-5073 (2015).
Taylor, R.G., et al., "*E. coli* host strains significantly affect the quality of small scale plasmid DNA preparations used for sequencing", Nucleic Acids Res. 21(7): 1677-1678 (1993).
Thermo Scientific, "Micrococcal Nuclease", 88216, 2 pages (2013).
Thiel, KW, et al., "Therapeutic Applications of DNA and RNA Aptamers", Oligonucleotides 19, 209-222 (2009).
Tiet, P, et al., "Colorimetric Detection of *Staphylococcus aureus* Contaminated Solutions without Purification", Bioconjugate Chem 28(1), 183-193 (2017).
Trevino, S, et al., "High-throughput bead-based identification of structure-switching aptamer beacons", Chembiochem 15, 1877-1881 (2014).
Ueno, et al., "Synthesis and properties of a novel molecular beacon containing a benzene-phosphate backbone at its stem moiety", Org. Biomol. Chem. 7, 2761-2769 (2009).
Van Hal, SJ, et al., "Predictors of mortality in *Staphylococcus aureus* Bacteremia.", Clin Microbiol Rev. vol. 25(2) p. 362-386 (2012).
Wannamaker, L, et al., "Streptococcal nucleases. II. Characterization of DNAse D", J Exp Med 126(3), 497-508 (1967).
Weissleder, R., et al., "In vivo imaging of tumors with protease-activated near-infrared fluorescent probes.", Nat Biotechnol. vol. 17(4) p. 375-378 (1999).
Weissleder, R, et al., "Shedding light onto live molecular targets", Nat Med 9(1), 123-128 (2003).
Whiteaker, J, et al., "Antibody-based enrichment of peptides on magnetic beads for mass-spectrometry-based quantification of serum biomarkers", Analytical Biochemistry 362, 44-54 (2007).
Wilson, M.L., et al., "Laboratory diagnosis of urinary tract infections in adult patients.", Clin Infect Dis. Vol. 38(8) p. 1150-1158 (2004).
Kiong, Y., et al., "Real-time in vivo bioluminescent imaging for evaluating the efficacy of antibiotics in a rat *Staphylococcus aureus* endocarditis model.", Antimicrob Agents Chemother. vol. 49(1) p. 380-387 (2005).

Zhao, et al., "Detection and quantitation of RNA base modifications", RNA 10, 996-1002 (2004).
Hernandez, F, et al., "Optical imaging of *S. aureus* infections with a quenched fluorescent oligonucleotide probe", Abstract presented in Boston, MA at the Annual Meeting of the Oligonucleotide-Therapeutics-Society on Oct. 28-31, 2012.
Hernandez, F, et al., "Optical imaging of *S. aureus* infections with a quenched fluorescent oligonucleotide probe", Presented Oct. 28-31, 2012 in Boston, MA at the Annual Meeting of the Oligonucleotide-Therapeutics-Society.
Holtze, C, et al., "Biocompatible surfactants for water-in-fluorocarbon emulsions", Lab Chip 8, 1632-1639 (2008).
Huang, et al., "A high sensitive and specific QDs FRET bioprobe for MNase", Chem Commun, 5990-5992 (2008).
Kaper, J.B., et al., "Pathogenic *Escherichia coli*.", Nat Rev Microbiol. vol. 2(2) p. 123-140 (2004).
Kelemen, B.R., et al., "Hypersensitive substrate for ribonucleases.", Nucleic Acids Res. vol. 27(18) p. 3696-3701 (1999).
Kiedrowski, M., et al., "Nuclease modulates biofilm formation in community-associated methicillin-resistant *Staphylococcus aureus*.", PLoS One. vol. 6(11) e26714 (2011).
Kiedrowski, et al., "*Staphylococcus aureus* Nuc2 is a Functional, Surface-Attached Extracellular Nuclease", PLOS One vol. 9 (4), E95574, 13 pages (2014).
Kim, S, et al., "Large-scale femtoliter droplet array for digital counting of single biomolecules", Lab Chip 12, 4986-4991 (2012).
Klevens, R., et al., "Invasive methicillin-resistant *Staphylococcus aureus* infections in the United States.", JAMA. vol. 298(15) p. 1763-1771 (2007).
Lachica, R, et al., "Metachromatic Agar-Diffusion Methods for Detecting Staphylococcal Nuclease Activity", Applied Microbiology 21(4), 585-587 (1971).
Lagace Wiens, "Thermostable DNase Is Superior to Tube Coagulase for Direct Detection of *Staphylococcus aurues* in Postive Blood Cultures", Journal of Clinical Microbiology 45(10), 3478-3479 (2007).
Lau, H., et al., "Identification of Klebsiella pneumoniae genes uniquely expressed in a strain virulent using a murine model of bacterial pneumonia.", Microb Pathog. vol. 42(4) p. 148-155 (2007).
Leevy, et al., "Optical Imaging of Bacterial Infection in Living Mice Using a Fluorescent Near-Infrared Molecular Probe", J. Am. Chem. Soc. 128, 16476-16477 (2006).
Lehman, I.R., et al., "The deoxyribonucleases of *Escherichia coli*. II. Purification and properties of a ribonucleic acid-inhibitable endonuclease.", J Biol Chem. vol. 237 p. 819-828 (1962).
Life Science Technologies, "The Digital PCR Revolution", www.Sciencemag.org/products, 212-214 (2014).
Livak, K, et al., "Oligonucleotides with Fluorescent Dyes at Opposite Ends Provide a Quenched Probe System Useful for Detecting PCR Product and Nucleic Acid Hybridization", PCR Methods and Applications 4, 357-362 (1995).
Ma, et al., "Real-time monitoring of restriction enjonuclease activity using molecular beacon", Analytical Biochemistry 363, 294 (2007).
Madison, B, et al., "Rapid Identification of *Staphylococcus aureus* in Blood Cultures by Thermonuclease Testing", Journal of Clinical Microbiology 18(3), 722-724 (1983).
McKenna, et al., "Purification and Properties of a Mammalian Endonuclease Showing Site-specific Cleavage of DNA", Journal of Biological Chemistry 256 (12), 6435 (1981).
McNamara, J, et al., "Degradation of Nuclease-Stabilized RNA Oligonucleotides in a Cell Culture Contaminated with Mycoplasma", 7th Annual Meeting of the Oligonucleotide-Therapeutics-Society, Abstract, Copenhagen, Denmark, Sep. 8-10, 2011.
McNamara, J, et al., "Degradation of Nuclease-Stabilized RNA Oligonucleotides in a Cell Culture Contaminated with Mycoplasma", Presented Sep. 8-10, 2011, in Copenhagen, Denmark, at the 7th Annual Meeting of the Oligonucleotide-Therapeutics-Society.
McNamara, et al., "Degradation of Nuclease-stabilized RNA Oligonucleotides in a cell culture contaminated with Mycoplasma", XP009183088, Poster Abstracts, 45, Nucleic Acid Therapeutics, vol. 21 (5), A21, 64 pages (2011).

(56) References Cited

OTHER PUBLICATIONS

McNamara, J, "Non-invasive Imaging of *S. aureus* Infections with a Nuclease-Activated Probe", Seminar at the 7th Edition of Nosocomial Infection Day, Lyon France, presented via Skype, Dec. 10, 2015.

McNamara, J, "Nuclease-activated probes for rapid, target-specific detection of bacterial pathogens", Presentation at Biological and Chemical Sensors Summit, 2016, La Jolla, CA, Dec. 6, 2016.

McNamara, J, "Nuclease-activated probes for rapid, target-specific detection of bacterial pathogens", Presentation at the Biodefense World Summit in Alexandria, VA. on Jun. 26-29, 2017.

McNamara, J, et al., "Optical imaging of *S. aureus* infections with a quenched fluorescent oligonucleotide probe", Presentation at RNAIowa meeting on campus on Oct. 25, 2012.

Mcnamara, J, "Rapid Nuclease-Based Assays for Infectious Diseases", Presented at the GTCBio Conference 7th Non-Coding RNA & RNAi Therapeutics Conference in Boston, MA on Sep. 14-15, 2016.

Miller, O, et al., "Directed evolution by in vitro compartmentalization", Nat Methods 3, 561-570 (2006).

Moon, A.F., et al., "Structural insights into catalytic and substrate binding mechanisms of the strategic EndA nuclease from *Streptococcus pneumoniae*.", Nucleic Acids Res. vol. 39(7) p. 2943-2953 (2011).

Moore, M, et al., "Protection of HIV Neutralizing Aptamers against Rectal and Vaginal Nucleases: Implications for RNA-Based Therapeutics", Journal of Biological Chemistry 286(4), 2526-2535 (2010).

Niu, C., et al., "Isolation and characterization of an autoinducer synthase from Acinetobacter baumannii.", J Bacteriol. vol. 190(9) p. 3386-3392 (2008).

Novick, R, "Genetic systems in staphylococci", Methods Enzymol 204, 587-636 (1991).

Patent Cooperation Treaty, International Searching Authority, Search Report and Written Opinion for PCT/US2018/053107, 10 pages, Jan. 25, 2019.

Pieken, et al., "Kinetic characterization of ribonuclease-resistant 2'-modified hammerhead ribozymes", Science 253, 314-317 (1991).

Rajendran, M, et al., "Selection of fluorescent aptamer beacons that light up in the presence of zinc", Anal Bioanal Chem 390, 1067-1075 (2008).

Ratner, H, et al., "Thermonuclease Test for Same-Day Identification of *Staphylococcus aureus* in Blood Cultures", Journal of Clinical Microbiology 21(6), 995-995 (1985).

Roach, L, et al., "Controlling nonspecific protein adsorption in a plug-based microfluidic system by controlling Interfacial chemistry using fluorous-phase surfactants", Anal Chem 77, 785-796 (2005).

Rondelez, Y, et al., "Microfabricated arrays of femtoliter chambers allow single molecule enzymology", Nat Biotechnol 23, 361-365 (2005).

Rosman, C, et al., "Ex Vivo Tracer Efficacy in Optical Imaging of *Staphylococcus aureus* Nuclease Activity", Scientific Reports 8, 1305, 8 pages (2018).

Rotman, B, "Measurement of activity of single molecules of beta-D-galactosidase", Proc Natl Acad Sci U S A 47, 1981-1991 (1961).

Ryckelynck, M, et al., "Using droplet-based microfluidics to improve the catalytic properties of RNA under multiple-turnover conditions", RNA 21, 458-469 (2015).

Sakakihara, S, et al., "A single-molecule enzymatic assay in a directly accessible femtoliter droplet array", Lab Chip 10, 3355-3362 (2010).

Schilcher, K., et al., "Increased neutrophil extracellular trap-mediated *Staphylococcus aureus* clearance through Inhibition of nuclease activity by clindamycin and immunoglobulin.", J Infect Dis. vol. 210(3) p. 473-482 (2014).

Schlievert, P., et al., "Endotoxin enhancement as a possible etiology of early-onset group B beta-hemolytic streptococcal sepsis in the newborn.", Obstet Gynecol. vol. 61(5) p. 588-592 (1983).

Shim, J, et al., "Ultrarapid generation of femtoliter microfluidic droplets for single-molecule-counting immunoassays", ACS Nano 7, 5955-5964 (2013).

Song, H, et al., "Millisecond kinetics on a microfluidic chip using nanoliters of reagents", J Am Chem Soc 125, 14613-14619 (2003).

Stoltz, DA, et al., "Cystic fibrosis pigs develop lung disease and exhibit defective bacterial eradication at birth", Sci Transl Med 2, 29ra31, 18 pages (2010).

Stover, C., et al., "Complete genome sequence of Pseudomonas aeruginosa PAO1, an opportunistic pathogen.", Nature vol. 406(6799) p. 959-964 (2000).

Straub, T.M., et al., "Towards a unified system for detecting waterborne pathogens.", J Microbiol Methods. vol. 53 (2) p. 185-197 (2003).

Anna, S, et al., "Formation of dispersions using "flow focusing" in microchannels", Applied Physics Letters 82(3), 364-366 (2003).

Arayanarakool, R, et al., "Single-enzyme analysis in a droplet-based micro- and nanofluidic system", Lab Chip 13, 1955-1962 (2013).

Asahara, H., "Purification and characterization of *Escherichia coli* endonuclease III from the cloned nth gene.", Biochemistry. vol. 28, No. (10) p. 4444-4449 (1989).

Baba, T., et al., "Construction of *Escherichia coli* K-12 in-frame, single-gene knockout mutants: the Keio collection", Mol Syst Biol. vol. 2: 2006.0008. (2006).

Baba, T., et al., "Genome sequence of *Staphylococcus aureus* strain Newman and comparative analysis of staphylococcal genomes: polymorphism and evolution of two major pathogenicity islands.", J Bacteriol. vol. 190(1) p. 300-310 (2008).

Balamurugan, S, et al., "Surface immobilization methods for aptamer diagnostic applications", Anal Bioanal Chem 390, 1009-1021 (2008).

Basu, A, "Digital Assays Part I: Partitioning Statistics and Digital PCR", SLAS Technol 22, 369-386 (2017).

Basu, A, "Digital Assays Part II: Digital Protein and Cell Assays", SLAS Technol 22, 387-405 (2017).

Beenken, K., et al., "Epistatic relationships between sarA and agr in *Staphylococcus aureus* biofilm formation.", PLoS One. vol. 5(5) e10790 (2010).

Behlke, MA, "Chemical modification of siRNAs for in vivo use", Oligonucleotides 18, 305-319 (2008).

Behlke, et al., "Designing Antisense Oligonucleotides", Integrated DNA Technologies, 1-17 (2005).

Bettegowda, et al., "Imaging bacterial infections with radiolabeled 1-(2'-deoxy-2-fluoro-betas-D-arabinofuranosyl)-5-iodouracil", PNAS 102 (4), 1145 (2005).

Biggins, et al., "A continuous assay for DNA cleavage: The application of "break lights" to enediynes, iron-dependent agents, and nucleases", PNAS 97 (25), 13537 (2000).

Blasco, et al., "Specific assays for bacteria using phage mediated release of adenylate kinase", Journal of Applied Microbiology 84, 661 (1988).

Borsa, B, et al., "*Staphylococcus aureus* detection in blood samples by silica nanoparticle-oligonucleotides conjugates", Biosens Bioelectron 86, 27-32 (2016).

Brakstad, O, et al., "Comparison of tests designed to identify *Staphylococcus aureus* thermostable nuclease", APMIS 103, 219 (1995).

Burghardt, E, et al., "Rapid, Culture-Free Detection of *Staphylococcus aureus* Bacteremia", PLoS One 11(6), e0157234 (2016).

Choppa, P.C., et al., "Multiplex PCR for the detection of Mycoplasma fermentans, M. hominis and M. penetrans in cell cultures and blood samples of patients with chronic fatigue syndrome.", Mol Cell Probes. vol. 12(5) p. 301-308 (1998).

Christensen, S, et al., "Mixing subattolitre vols. in a quantitative and highly parallel manner with soft matter hanofluidics", Nat Nanotechnol 7, 51-55 (2012).

Connelly, J.T., et al., "Biosensors for the detection of waterborne pathogens.", Anal Bioanal Chem. vol. 402(1), 117-127 (2012).

Crooke, et al., "Kinetic characteristics of *Escherichia coil* RNase H1: cleavage of various antisense oligonucleotide-RNA dupleses", Biochem J 312, 599-608 (1995).

(56) References Cited

OTHER PUBLICATIONS

Cruz, et al., "Dinucleotide Junction Cleavage Versatility of 8-17 Deoxyribozyme", Chemistry and Biology 11, 57 (2004).

Cuatrecasas, P., et al., "Catalytic properties and specificity of the extracellular nuclease of *Staphylococcus aureus*.", J Biol Chem. vol. 242(7) p. 1541-1547 (1967).

Dickey, D, et al., "Rapid and Sensitive Detection of Circulating Tumor Cells with Nuclease-Activated Oligonucleotide Probes", 18th Annual Meeting of the American-Society-of-Gene-and-Cell-Therapy (ASGCT), New Orleans, LA, May 13-16, 2015, published in Molecular Therapy, 23, pp. S28-S28, Supp: 1, Meeting Abstract: 63, Published: May 2015.

Diehl, F, et al., "BEAMing: single-molecule PCR on microparticles in water-in-oil emulsions", Nature Methods 3(7), 551-559 (2006).

DNASEALERT, QC System, Instruction Manual, 22 pages (2009).

Dressman, D, et al., "Transforming single DNA molecules into fluorescent magnetic particles for detection and enumeration of genetic variations", Proc Natl Acad Sci U S A 100, 8817-8822 (2003).

Eisenschmidt, et al., "A fluorimetric assay for on-line detection of DNA cleavage by restriction endonucleases", Journal of Biotechnology 96, 185 (2002).

English, B, et al., "Ever-fluctuating single enzyme molecules: Michaelis-Menten equation revisited", Nat Chem Biol 2, 87-94 (2006).

Eskine, et al., "Interactions of the EcoRV restriction endonuclease with fluorescent oligodeoxynucleotides", Gene 157, 153 (1995).

Ferrieri, P, et al., "Biochemical and immunological characterization of the extracellular nucleases of group B streptococci", J Exp Med 151(1), 56-68 (1980).

Ferrieri, P, et al., "Production of bacteremia and meningitis in infant rats with group B streptococcal serotypes", Infect Immun 27(3), 1023-1032 (1980).

Flenker, K, et al., "Rapid Detection of Urinary Tract Infections via Bacterial Nuclease Activity", Molecular Therapy 25(6), 1353-1362 (2017).

Foxman, B., et al., "Epidemiology of urinary tract infections: incidence, morbidity, and economic costs.", Am J Med. vol. 113 Suppl 1A p. 5S-13S (2002).

Foxman, B., "The epidemiology of urinary tract infection.", Nat Rev Urol. Vol.7(12) p. 653-660 (2010).

Fraser, L, et al., "Oligonucleotide Functionalised Microbeads: Indispensable Tools for High-Throughput Aptamer Selection", Molecules 20, 21298-21312 (2015).

Ghosh, et al., "Real time kinetics of restriction endonuclease cleavage monitored by fluorescence resonance energy transfer", Nucleic Acids Research 22 (15), 3155 (1994).

Giangrande, P, et al., "Nuclease-activated oligonucleotide probes for detection of breast cancer circulating tumor cells (CTCs): Early clinical results", Early clinical results [abstract]. In: Proceedings of the 2016 San Antonio Breast Cancer Symposium; San Antonio, TX. Philadelphia (PA), Dec. 6-10, 2016: AACR; Cancer Res 2017;77(4 Suppl): Abstract nr P1-01-14.

Gillaspy, A., et al., "Role of the accessory gene regulator (agr) in pathogenesis of staphylococcal osteomyelitis.", Infect Immun. vol. 63(9) p. 3373-3380 (1995).

Goodridge, et al., "Development and Characterization of a Fluorescent-Bacteriophage Assay for Detection of *Escherichia coli* O157:H7", Applied and Environmental Microbiology 65 (4), 197 (1999).

Graham, et al., "Gene repair and mutagenesis mediated by chimeric RNA-DNA oligonucleotides: chimeraplasty for gene therapy and conversion of single nucleotide polymorphisms (SNP)s)", Biochimica et Biophysica Acta 1587, 1-6 (2002).

Green, L, et al., "Nuclease-resistant nucleic acid ligands to vascular permeability factor/vascular endothelial growth factor", Chem Biol 2(10), 683-695 (1995).

Guan, Z, et al., "A highly parallel microfluidic droplet method enabling single-molecule counting for digital enzyme detection", Biomicrofluidics 8, 014110, 13 pages (2014).

Guo, G., et al., "nfi, the gene for endonuclease V in *Escherichia coli* K-12.", J Bacteriol. vol. 179, No.(2) p. 310-316 (1997).

Harrington, et al., "The characterization of a mammalilan DNA structure-specific endonuclease", The EMBO Journal 13 (5), 1235 (1994).

Heilbronner, S., et al., "Genome sequence of *Staphylococcus lugdunensis* N920143 allows identification of putative colonization and virulence factors.", FEMS Microbiol Lett. vol. 322(1) p. 60-67 (2011).

Hernandez, F, et al., "Degradation of nuclease-stabilized RNA oligonucleotides in Mycoplasma-contaminated cell culture media", Nucleic Acid Ther 22, 58-68 (2012).

Hernandez, F, et al., "NanoKeepers: stimuli responsive nanocapsules for programmed specific targeting and drug delivery", Chemical Communications 50(67), 9489-9492 (2014).

Hernandez, F, et al., "Noninvasive imaging of *Staphylococcus aureus* infections with a nuclease-activated probe", Nat Med 20(3), 301-306 (2014).

Hernandez, L, et al., "Nuclease activity as a specific biomarker for breast cancer", Chem Commun 52(83), 12346-12349 (2016).

Spangler, R., et al., "Optimizing Taq Polymerase Concentration for Improved Signal-to-Noise in the Broad Range Detection of Low Abundance Bacteria", PLoS One 4 (9), e7010, 9 pages (2009).

\* cited by examiner

After Incubation

Oil

Figure 11

Poisson Distribution Modeling of MN Molecules Among Droplets

Probability of droplets having x number of MN molecules is $f(x) = \dfrac{\mu^x e^{-\mu}}{x!}$ where $\mu$ is the mean number of MN molecules per droplet.

$$f(0) = 0.135 = \dfrac{\mu^0 e^{-\mu}}{0!} = \dfrac{1 e^{-\mu}}{1!} = e^{-\mu}$$

$$\ln(0.135) = -\mu = -2 \longrightarrow \mu = 2$$

$$f(1) = \dfrac{2^1 e^{-2}}{1!} = 0.27 \qquad f(5) = \dfrac{2^5 e^{-2}}{5!} = 0.036$$

$$f(2) = \dfrac{2^2 e^{-2}}{2!} = 0.27 \qquad f(6) = \dfrac{2^6 e^{-2}}{6!} = 0.012$$

$$f(3) = \dfrac{2^3 e^{-2}}{3!} = 0.18 \qquad f(7) = \dfrac{2^7 e^{-2}}{7!} = 0.0034$$

$$f(4) = \dfrac{2^4 e^{-2}}{4!} = 0.09 \qquad f(8) = \dfrac{2^8 e^{-2}}{8!} = 0.00086$$

Figure 12

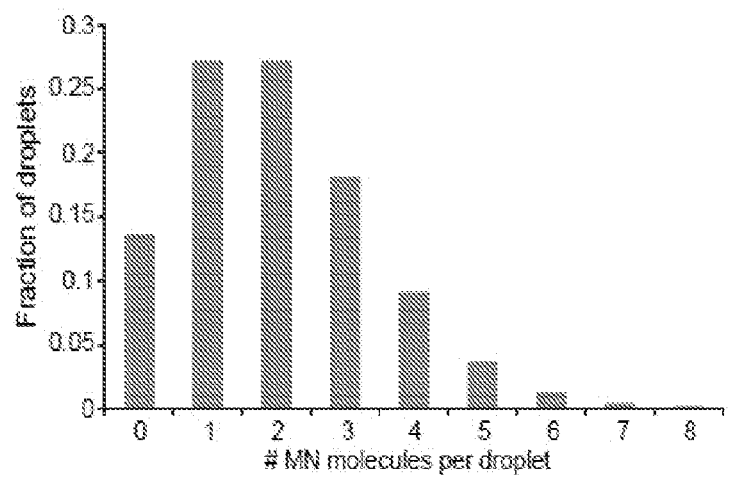

SEQUENCE LISTING

<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt t                                                          11

<210> SEQ ID NO 2

<400> SEQUENCE: 2

000

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 tggatcca                                                               8

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actacgtagt cacaactacg tagt                                            24

DIGITAL NUCLEASE DETECTION COMPOSITIONS AND METHODS

PRIORITY APPLICATION

This application claims priority to U.S. Provisional Application No. 62/565,674 that was filed on Sep. 29, 2017. The entire contents of the application referenced above is hereby incorporated by reference herein.

STATEMENT REGARDING FEDERALLY SPONSORED RESEARCH

This invention was made with government support under R01 AI106738 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 29, 2018, is named 17023_216WO1_SL.txt and is 1,039 bytes in size.

BACKGROUND OF THE INVENTION

Chemical moieties that quench fluorescent light operate through a variety of mechanisms, including fluorescence resonance energy transfer (FRET) processes and ground state quenching. FRET is one of the most common mechanisms of fluorescent quenching and can occur when the emission spectrum of the fluorescent donor overlaps the absorbance spectrum of the quencher and when the donor and quencher are within a sufficient distance known as the Forster distance. The energy absorbed by a quencher can subsequently be released through a variety of mechanisms depending upon the chemical nature of the quencher. Captured energy can be released through fluorescence or through nonfluorescent mechanisms, including charge transfer and collisional mechanisms, or a combination of such mechanisms. When a quencher releases captured energy through nonfluorescent mechanisms FRET is simply observed as a reduction in the fluorescent emission of the fluorescent donor.

Although FRET is the most common mechanism for quenching, any combination of molecular orientation and spectral coincidence that results in quenching is a useful mechanism for quenching by the compounds of the present invention. For example, ground-state quenching can occur in the absence of spectral overlap if the fluorophore and quencher are sufficiently close together to form a ground state complex.

Quenching processes that rely on the interaction of two dyes as their spatial relationship changes can be used conveniently to detect and/or identify nucleotide sequences and other biological phenomena. As noted previously, the energy transfer process requires overlap between the emission spectrum of the fluorescent donor and the absorbance spectrum of the quencher. This complicates the design of probes because not all potential quencher/donor pairs can be used. For example, the quencher BHQ-1, which maximally absorbs light in the wavelength range of about 500-550 nm, can quench the fluorescent light emitted from the fluorophore fluorescein, which has a wavelength of about 520 nm. In contrast, the quencher BHQ-3, which maximally absorbs light in the wavelength range of about 650-700 nm would be less effective at quenching the fluorescence of fluorescein but would be quite effective at quenching the fluorescence of the fluorophore Cy5 which fluoresces at about 670 nm. The use of varied quenchers complicates assay development because the purification of a given probe can vary greatly depending on the nature of the quencher attached.

Many quenchers emit energy through fluorescence reducing the signal to noise ratio of the probes that contain them and the sensitivity of assays that utilize them. Such quenchers interfere with the use of fluorophores that fluoresce at similar wavelength ranges. This limits the number of fluorophores that can be used with such quenchers thereby limiting their usefulness for multiplexed assays that rely on the use of distinct fluorophores in distinct probes that all contain a single quencher.

Single molecule detection of enzymes, including beta-galactosidase, horse-radish peroxidase, F1-ATPase, beta-glucosidase and alkaline phosphatase using femtoliter or picoliter-scale partitions (such as water-in-oil emulsions) has previously been demonstrated (See, Basu, A. S. (2017b). Digital Assays Part II: Digital Protein and Cell Assays. SLAS Technol 22, 387-405). The fluorogenic substrates used in these studies are small molecules such as fluorescein di-β-d-galactopyranoside (FDG).

Endonucleases (e.g., certain ribonucleases and deoxyribonucleases) are enzymes that cleave the phosphodiester bond within a polynucleotide (DNA or RNA) chain, in contrast to exonucleases, which cleave phosphodiester bonds at the end of a polynucleotide chain. Typically, a restriction site, i.e., a recognition site for a class of endonucleases known as restriction enzymes, is a palindromic sequence four to six nucleotides long (e.g., TGGATCCA, SEQ ID NO:3).

Restriction enzymes, found in bacteria and archaea, are thought to have evolved to provide a defense mechanism against invading viruses. Inside a bacterial host, the restriction enzymes selectively cut up foreign DNA in a process called restriction; host DNA is methylated by a modification enzyme (a methylase) to protect it from the restriction enzyme's activity. Collectively, these two processes form the restriction modification system. To cut the DNA, a restriction enzyme makes two incisions, once through each sugar-phosphate backbone (i.e. each strand) of the DNA double helix.

Some cells secrete copious quantities of non-specific RNases such as A and T1. RNases are extremely common, resulting in very short lifespans for any RNA that is not in a protected environment. Similar to restriction enzymes, which cleave highly specific sequences of double-stranded DNA, a variety of endoribonucleases that recognize and cleave specific sequences of single-stranded RNA have been recently classified.

Nuclease reaction kinetics are non-linear, making it difficult to quantify nuclease concentrations. Nuclease activity declines over time, allowing background signal from undigested probe to mask the signal. In addition, error in the curve makes quantification difficult. Accordingly, there is a need for ultrasensitive molecular detection technologies capable of precise quantification of target molecules.

SUMMARY OF THE INVENTION

In certain embodiments, the present invention provides a means of quantifying nuclease concentrations without using a standard curve. Benefits from this method include single nuclease molecule sensitivity; a binary output, instead of a continuum; a higher concentration of digested substrates; the beads prevent diffusion of signal; and there is no need for the generation of a standard curve.

A detection composition comprising a picodroplet comprising (a) an aqueous solution lacking magnesium and/or comprising a divalent cation chelator, and (b) a substrate probe comprising (i) an oligonucleotide of 2-75 nucleotides in length, (ii) a fluorophore operably linked to the oligonucleotide, and (iii) a quencher operably linked to the oligonucleotide.

In certain embodiments, the present invention provides a method of detecting at least one individual nuclease molecule present in a sample, (a) contacting an aqueous sample suspected of containing at least one nuclease molecule with at least one detection composition to form an aqueous reaction mixture, wherein the detection composition comprises a picodroplet comprising an aqueous solution and a substrate probe operably linked to a magnetic microbead, and wherein the substrate probe comprises (i) an oligonucleotide of 2-75 nucleotides in length, (ii) a fluorophore operably linked to the oligonucleotide in a configuration that will result in continued linkage of the fluorophore to the microbead upon enzymatic cleavage of the oligonucleotide, and (iii) a quencher operably linked to the oligonucleotide in a configuration that will result in its release from the microbead upon enzymatic cleavage of the oligonucleotide, (b) emulsifying the aqueous mixture in oil to form picoliter-scale droplets in an emulsion, (c) incubating the picoliter-scale droplets in the emulsion in order for the nuclease, if present, to digest the substrate probes linked to the microbeads, (d) recovering the microbeads, and (e) detecting fluorescence emitting from the microbeads.

BRIEF DESCRIPTION OF DRAWINGS

FIG. 1 discloses "TTTTTTTTTTT" as SEQ ID NO: 1.

FIG. 2 discloses SEQ ID NO: 1.

FIG. 4 discloses "TTTTTTTTTTT" as SEQ ID NO: 1.

FIG. 5 discloses "TTTTTTTTTTT" as SEQ ID NO: 1.

FIG. 7 discloses "TTTTTTTTTTT" as SEQ ID NO: 1.

FIG. 11. Poisson distribution modeling of MN molecules among droplets.

FIG. 12. Poisson distribution of MN across the droplets of an emulsion in which 13.5% of beads were unactivated. The concentration of nuclease can be calculated directly (i.e., a standard curve of titrated nuclease is not needed).

DETAILED DESCRIPTION OF THE INVENTION

Figure 1:
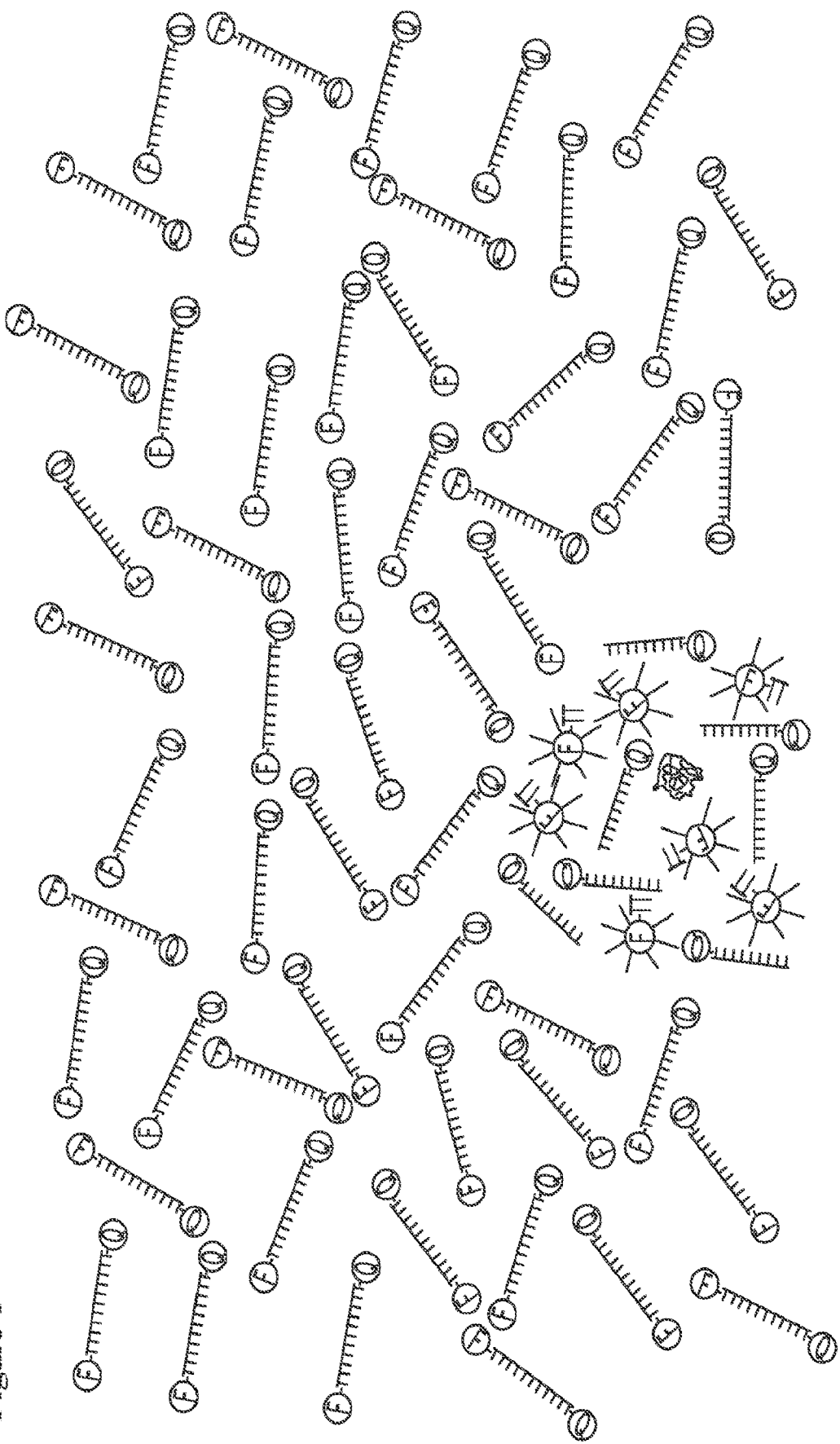
FIG. 1. Depiction of probe digestion by dilute nucleases.

There is currently a need for ultrasensitive molecular detection technologies capable of precise quantification of target molecules. For instance, the detection and quantitation of molecular targets of microbial pathogens in biological fluids can be used to determine whether a patient has an infection with a particular microbe. Quantification is needed to determine the level of pathogen present, an important piece of data that can distinguish background from clinically significant levels. There are similar applications for pathogen detection in food (e.g., *Salmonella* and *E. coli* detection) and for bioterrorism. Ultrasensitive detection methods primarily depend on enzymatic amplification steps that are inherently non-linear and therefore require the parallel evaluation of serially diluted standards (standard curves) for accurate interpretation. This added burden is avoided with digital droplet or emulsion PCR based methods that can precisely quantify target DNA sequences without standard curves. The present invention leverages the precise standard curve-independence of digital PCR, but is capable of detecting nucleases, an alternative category of target molecule. Because nucleases are substantially more abundant than DNA sequences, the present invention yields greater sensitivity for target microbial pathogens than PCR, currently the most sensitive platform technology. Furthermore, the present invention is substantially less complex than digital PCR, which requires complex reaction mixtures and sophisticated temperature cycling instruments, neither of which is needed for nuclease detection. Altogether, the digital nuclease detection approach has the potential to be a superior alternative for a variety of valuable applications.

Experiments have been performed providing data demonstrating the feasibility of the method in a format that includes quenched fluorescent probes attached to magnetic beads. The beads are suspended in an aqueous phase that includes nucleases in a reaction buffer. This solution is emulsified in oil to create thousands of very small reactions. After the reactions have progressed, the beads are recovered and their fluorescence is measured with flow cytometry. Two distinct populations of beads can be seen. Those with elevated fluorescence and those with basal levels of fluorescence.

Anticipated fields of application include infectious disease diagnostics, pathogen detection in food and bioterrorism detection. This invention overcomes two important problems. It provides a means for detecting single molecules of target nucleases, whereas previous methods cannot detect fewer than several hundred. It also provides a simple means of quantifying the number of target nuclease molecules that exists in a sample; this approach does not require a standard curve.

The present approach can also be used to quantify precisely the number of nuclease molecules expressed per cell. For instance, nucleases can be expressed from plasmid or other vectors in cells and the number of nucleases expressed per number of cells can be precisely quantified. The sensitivity of the present invention enables this on the single-cell level (i.e., single-cell analysis of protein expression on single cells isolated with established methods such as microfluidic isolation). In other words, nucleases are used as expression reporters. In contrast to semi-quantitative methods in common use for measuring protein expression (e.g., western blot, ELISA), the present approach is quantitative and can be easily multiplexed by tailoring distinct probes to distinct enzymes. For example, restriction enzyme recognition site are incorporated into probes (with distinct fluorophores) and then reporters consisting of the corresponding enzymes are used to report expression driven by distinct promoters.

In certain embodiments, the invention is a process, but also includes novel oligonucleotide probes and compositions. In certain embodiments, the invention comprises a process in which a nuclease reaction is divided into many thousands of parallel aqueous phase reactions of approximately 10 picoliters or less, that are isolated from one another due to their presence in a water-in-oil emulsion. The substrate is a quenched fluorescent oligonucleotide probe that is activated upon digestion yielding an increase in fluorescence. Upon completion of the reaction step, the fluorescence of the individual reactions is measured. If the nuclease is present in very dilute concentrations, each reaction will contain either 0, 1 or in rare cases, more than 1 nuclease molecule. If the sensitivity is high enough, a single nuclease molecule will produce elevated fluorescence. This enables the resulting reactions to be divided into those that have one or more nuclease molecule and those that do not (i.e., a digital endpoint). Assuming a random distribution of nuclease molecules, the nucleases will exhibit a Poisson distribution among the reactions. Fitting a Poisson model to the digital reaction results can thus be used to determine the number of nuclease molecules in the sample that was used as input, without the need for a standard curve.

In certain embodiments, the present invention utilizes a quenched fluorescent oligonucleotide substrate, many copies of which are immobilized on streptavidin-coupled magnetic beads. The oligo sequence and composition is as follows: Biotin-Cy5-TTTTTTTTTTT-ZEN-RQ (SEQ ID NO: 1), where Biotin is the streptavidin binding moiety, Cy5 is a fluorophore, T is the deoxythymidine (DNA) nucleotide, ZEN is the IDT Zen quencher and RQ is the IDT Iowa Black RQ quencher. In certain embodiments, the oligo sequence and composition is as follows: Cy5-TTTTTTTTTTT-ZEN-RQ-Biotin (SEQ ID NO: 1). Upon incubation of oligo-coupled beads with micrococcal nuclease (MN), a secreted nuclease of $S.\ aureus$ that can efficiently digest poly T oligos, the beads exhibit a strong increase in fluorescence that can be measured with a fluorescence plate-reader and with fluorescence microscopy. Combining oligo-coupled beads with various concentrations of micrococcal nuclease in reaction buffer and immediately emulsifying the reactions in oil produced many thousands of aqueous reaction droplets that can be seen with a microscope.

The aqueous droplets of most emulsions contain on average either no beads or only a single bead, as can be confirmed with microscopy. These emulsions are stable and were incubated at room temperature and at 37° C. for different lengths of time. After several hours at 37° C., beads recovered from reactions in which approximately 163 MN molecules will exist per reaction (assuming random distribution) exhibited uniformly elevated fluorescence. Progressively lower concentrations produced uniformly elevated fluorescence, but lower fluorescence levels (i.e., beads were brighter than undigested beads, but not as bright as completely digested beads). Finally, incubation of oligo-coupled beads with a dilute MN concentration that on average will yield reactions with only a single MN molecule or no MN molecule produced two distinct populations of fluorescent beads, some with elevated fluorescence and some with basal levels. This can be seen with fluorescence microscopic images and with flow cytometry (2 distinct peaks are clear). The result with this last sample indicates that single molecules of MN are able to produce detectable fluorescence in this format and that the format produces the sought after digital readout for the population of reactions.

In certain embodiments, the present invention provides short oligonucleotide probes (Substrates) composed of chemically modified DNA or RNA flanked with at least one fluorophore on one end and at least one fluorescence quencher on the other end. Upon cleavage of the probes by nucleases (e.g., an endonuclease), the fluorophore diffuses away from the quencher and exhibits fluorescence. The probes can thus be used to detect the presence of nucleases in biological samples such as blood, serum, plasma, stool, sweat, skin extracts, cell cultures, and food, and in vivo, and in environmental samples, such as water.

The oligonucleotide probe of the invention comprises a fluorescent reporter group and a quencher group in such physical proximity that the fluorescence signal from the reporter group is suppressed by the quencher group. Cleavage of the probe with a nuclease (e.g., endonuclease) enzyme leads to strand cleavage and physical separation of the reporter group (fluorophore) from the quencher group. Separation of reporter and quencher eliminates quenching, resulting in an increase in fluorescence emission from the reporter group. When the quencher is a so-called "dark quencher," the resulting fluorescence signal can be detected by direct visual inspection (using a microscope and an illumination source with a suitable wavelength, provided the emitted light includes visible wavelengths). Cleavage of the Substrate compositions described in the present invention can also be detected by fluorometry.

In one embodiment, the synthetic Substrate is an oligonucleotide comprising ribonucleotide residues. The synthetic Substrate can also be a chimeric oligonucleotide comprising RNase-cleavable, e.g., RNA residues, or modified RNase-resistant RNA residues. In certain embodiments, Substrate composition is such that cleavage is a ribonuclease-specific event and that cleavage by enzymes that are strictly deoxyribonucleases does not occur.

In one embodiment, the synthetic Substrate is a chimeric oligonucleotide comprising ribonucleotide residue(s) and modified ribonucleotide residue(s). In one embodiment, the synthetic Substrate is a chimeric oligonucleotide comprising ribonucleotide residues and 2'-O-methyl ribonucleotide residues. In one embodiment, the synthetic Substrate is a chimeric oligonucleotide comprising 2'-O-methyl ribonucleotide residues and one or more of each of the four ribonucleotide residues, adenosine, cytosine, guanosine, and uridine. Inclusion of the four distinct ribonucleotide bases in a single Substrate allows for detection of an increased spectrum of endonuclease enzyme activities by a single Substrate oligonucleotide.

In one embodiment, the synthetic Substrate is an oligonucleotide comprising deoxyribonucleotide residues. The synthetic Substrate can also be a chimeric oligonucleotide comprising DNase-cleavable, e.g., DNA, residues, or modified RNase-resistant RNA residues. Substrate composition is such that cleavage is a deoxyribonuclease-specific event and that cleavage by enzymes that are strictly ribonucleases does not occur.

In one embodiment, the synthetic Substrate is a chimeric oligonucleotide comprising deoxyribonucleotide residue(s) and modified ribonucleotide residue(s). In one embodiment, the synthetic Substrate is a chimeric oligonucleotide comprising deoxyribonucleotide residues and 2'-O-methyl ribonucleotide residues. In one embodiment, the synthetic Substrate is a chimeric oligonucleotide comprising 2'-O-methyl ribonucleotide residues and one or more of each of the four deoxyribonucleotide residues, deoxyadenosine, deoxycytosine, deoxyguanosine, and deoxythymidine. Inclusion of the four distinct deoxyribonucleotide bases in a single Substrate allows for detection of an increased spectrum of deoxyribonuclease enzyme activities by a single Substrate oligonucleotide.

To enable visual detection methods, the quenching group is itself not capable of fluorescence emission, being a "dark quencher". Use of a "dark quencher" eliminates the background fluorescence of the intact Substrate that would otherwise occur as a result of energy transfer from the reporter fluorophore. In one embodiment, the fluorescence quencher comprises dabcyl (4-(4'-dimethylaminophenylazo) benzoic acid). In one embodiment, the fluorescence quencher is comprised of QSY™-7 carboxylic acid, succinimidyl ester (N,N'-dimethyl-N,N'-diphenyl-4-((5-t-butoxycarbonylaminopentyl)aminocarbon yl) piperidinylsulfonerhodamine; a diarylrhodamine derivative from Molecular Probes, Eugene, Oreg.). Any suitable fluorophore may be used as reporter provided its spectral properties are favorable for use with the chosen quencher. A variety of fluorophores can be used as reporters, including but not limited to, fluorescein, tetrachlorofluorescein, hexachlorofluorescein, rhodamine, tetramethylrhodamine, Cy-dyes, Texas Red, Bodipy dyes, and Alexa dyes.

With respect to the fluorescence quenching group, any compound that is a dark quencher can be used in the methods and compositions of the invention. Numerous compounds are capable of fluorescence quenching, many of which are not themselves fluorescent (i.e., are dark quenchers.) In one embodiment, the fluorescence-quenching group is a nitrogen-substituted xanthene compound, a substituted 4-(phenyldiazenyl)phenylamine compound, or a substituted 4-(phenyldiazenyl)naphthylamine compound. In certain specific modes of the embodiment, the fluorescence-quenching group is 4-(4'-dimethylaminophenylazo)benzoic acid), N,N'-dimethyl-N,N'-diphenyl-4-((5-t-butoxycarbonylaminopentyl) aminocarbonyl) piperidinylsulfonerhodamine (sold as QSY-7™ by Molecular Probes, Eugene, Oreg.), 4',5'-dinitrofluorescein, pipecolic acid amide (sold as QSY-33™ by Molecular Probes, Eugene, Oreg.) 4-[4-nitrophenyldiazinyl]phenylamine, or 4-[4-nitrophenyldiazinyl]naphthylamine (sold by Epoch Biosciences, Bothell, Wash.). In other specific modes of the embodiment, the fluorescence-quenching group is Black-Hole Quenchers™ 1, 2, or 3 (Biosearch Technologies, Inc.).

In certain embodiments, the fluorescence reporter group is fluorescein, tetrachlorofluorescein, hexachlorofluorescein, rhodamine, tetramethylrhodamine, a Cy dye, Texas Red, a Bodipy dye, or an Alexa dye.

With respect to the foregoing methods and compositions, the fluorescence reporter group or the fluorescence quenching group can be, but is not necessarily, attached to the 5'-terminal nucleotide of the substrate.

The nucleic acids of the invention, including those for use as substrates in the methods of the invention, in certain embodiments are single-stranded RNA molecule. In other embodiments, the nucleic acids of the invention are chimeric oligonucleotides comprising a nuclease resistant modified ribonucleotide residue. Exemplary RNase resistant modified ribonucleotide residues include 2'-O-methyl ribonucleotides, 2'-methoxyethoxy ribonucleotides, 2'-O-allyl ribonucleotides, 2'-O-pentyl ribonucleotides, 2'-O-butyl ribonucleotides, 2'-fluoro ribonucleotides, locked nucleic acid (LNA) nucleotides, unlocked nucleic acid (UNA) nucleotides, branched nucleic acid (BNA) nucleotides and 2'-fluoro-β-D-arabinonucleotides (FANA). In one mode of the embodiment, the modified ribonucleotide residue is at the 5'-terminus or the 3'-terminus of the cleavage domain. In yet other embodiments, the nucleic acids of the invention are chimeric oligonucleotides comprising a deoxyribonuclease resistant modified deoxyribonucleotide residue. In specific modes of the embodiments, the deoxyribonuclease resistant modified nucleotide residue is a phosphotriester deoxyribonucleotide, a methylphosphonate deoxyribonucleotide, a phosphoramidate deoxyribonucleotide, a phosphorothioate deoxyribonucleotide, a phosphorodithioate deoxyribonucleotide, or a boranophosphate deoxyribonucleotide, a 2'-O-methyl ribonucleotide, a 2'-methoxyethoxy ribonucleotide, a 2'-O-allyl ribonucleotide, a 2'-O-pentyl ribonucleotide, a 2'-O-butyl ribonucleotide, a 2'-fluoro ribonucleotide, a locked nucleic acid (LNA) nucleotide, an unlocked nucleic acid (UNA) nucleotide, a branched nucleic acid (BNA) nucleotide or a 2'-fluoro-β-D-arabinonucleotide (FANA). In yet other embodiments of the invention, the nucleic acids of the invention comprise a ribonuclease-cleavable modified ribonucleotide residue.

The nucleic acids of the invention, including those for use as substrates in the methods of the invention, are at least 2 nucleotides in length, such as 2 to 75 nucleotides in length. In certain specific embodiments, the nucleic acids of the invention are 5 to 20, 5 to 15, 5 to 10, 7 to 20, 7 to 15 or 7 to 10 nucleotides in length.

In certain embodiments, the fluorescence-quenching group of the nucleic acids of the invention is 5' to the cleavage domain and the fluorescence reporter group is 3' to the cleavage domain. In a specific embodiment, the fluorescence-quenching group is at the 5' terminus of the substrate. In another specific embodiment, the fluorescence reporter group is at the 3' terminus of the substrate.

In certain embodiments, the fluorescence reporter group of the nucleic acids of the invention is 5' to the cleavage domain and the fluorescence-quenching group is 3' to the cleavage domain. In a specific embodiment, the fluorescence reporter group is at the 5' terminus of the substrate. In another specific embodiment, the fluorescence-quenching group is at the 3' terminus of the substrate.

In one embodiment of the invention, a nucleic acid of the invention comprising the formula: 5'-$N_1$-n-$N_2$-3', wherein: (a) "$N_1$" represents zero to five 2'-modified ribonucleotide residues; (b) "$N_2$" represents zero to five 2'-modified ribonucleotide residues; and (c) "n" represents one to ten, such as four to ten unmodified ribonucleotide residues. In a certain specific embodiment, "$N_1$" represents one to five 2'-modified ribonucleotide residues. In certain modes of the embodiment, the fluorescence-quenching group or the fluorescent reporter group is attached to the 5'-terminal 2'-modified ribonucleotide residue of $N_1$.

In the nucleic acids of the invention, including nucleic acids with the formula: 5'-$N_1$-n-$N_2$-3', the fluorescence-quenching group can be 5' to the cleavage domain and the fluorescence reporter group is 3' to the cleavage domain; alternatively, the fluorescence reporter group is 5' to the cleavage domain and the fluorescence-quenching group is 3' to the cleavage domain.

"Probe" or "Substrate" Oligonucleotides

Compositions of the invention comprise synthetic oligonucleotide Substrates that are substrates for nuclease (e.g., endonuclease) enzymes. Substrate oligonucleotides of the invention comprise: 1) one or more nuclease-cleavable bases, e.g., RNA bases, some or all of which function as scissile linkages, 2) a fluorescence-reporter group and a fluorescence-quencher group (in a combination and proximity that permits optical FRET-based fluorescence quenching (and unquenching) detection methods), and 3) may optionally contain RNase-resistant modified RNA bases, nuclease-resistant DNA bases, or unmodified DNA bases. Synthetic oligonucleotide RNA-DNA chimeras wherein the internal RNA bonds function as a scissile linkage are described in U.S. Pat. Nos. 6,773,885 and 7,803,536. The fluorescence-reporter group and the fluorescence-quencher group are separated by at least one RNAse-cleavable residue, e.g., RNA base. Such residues serve as a cleavage domain for endonucleases (e.g, ribonucleases).

In certain embodiments, the substrate oligonucleotide probes are single-stranded or double-stranded oligoribonucleotides. In certain embodiments, the oligonucleotide probes are composed of modified oligoribonucleotides. The term "modified" encompasses nucleotides with a covalently modified base and/or sugar. For example, modified nucleotides include nucleotides having sugars that are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose. In certain embodiments, the Substrate includes, but is not limited to, 2'-O-methyl RNA, 2'-methoxyethoxy RNA, 2'-O-allyl RNA, 2'-O-pentyl RNA, and 2'-O-butyl RNA. In certain embodiments, the substrate is an RNA-2'-O-methyl RNA oligonucleotide having the general structure 5' r-NnN-q 3', where 'N' represents from about one to five 2'-modified ribonucleotide residues, 'n' represents one to ten unmodified ribonucleotide residues, r represents a fluorescence reporter group, and q' represents a fluorescence quencher group. The 5'- and 3'-position of reporter and quencher are interchangeable. In one embodiment, the fluorescence reporter group and the fluorescence quencher group are positioned at or near opposing ends of the molecule. It is not important which group is placed at or near the 5'-end versus the 3'-end. It is not required that the reporter and quencher groups be end modifications, however positioning these groups at termini simplifies manufacture of the Substrate. The fluorescence reporter group and the fluorescence quencher group may also be positioned internally so long as an RNA scissile linkage lies between reporter and quencher.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methyl cytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The oligonucleotides of the invention are synthesized using conventional phosphodiester linked nucleotides and synthesized using standard solid or solution phase synthesis techniques that are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the oligonucleotides have additional modifications, such as 2'O-methyl modification of the pyrimidines. In other embodiments, all of the nucleotides in the oligonucleotides are 2'O-methyl modified. Alternatively, the pyrimidines, or all the nucleotides, may be modified with 2'fluoros (both pyrimidines and purines).

The oligonucleotides are short, such as between 2-30 nucleotides in length (or any value in between). In certain embodiments, that oligonucleotide is between 8-15 nucleotides in length. In certain embodiments, that oligonucleotide is between 11-13 nucleotides in length. In general, shorter sequences will give better signal to noise ratios than longer probes and will therefore be more sensitive. However, in certain embodiments, shorter probes might not be the best substrate for the nuclease, so some degree of empiric optimization for length is needed. In certain embodiments, the oligonucleotide comprises 0-100% purines (or any value in between). In certain embodiments, the oligonucleotide comprises 100% pyrimidines.

It should be noted that the specific sequence of the oligonucleotide is not critical. Certain combinations of purines and pyrimidines are susceptible to bacterial endonucleases, while resisting mammalian nucleases. Endonucleases are enzymes that cleave the phosphodiester bond within a polynucleotide chain, in contrast to exonucleases, which cleave phosphodiester bonds at the end of a polynucleotide chain. Many bacterial nucleases are not sequence-specific like restriction enzymes, which typically require a recognition site and a cleavage pattern. Some endonucleases cleave single-stranded nucleic acid molecules, while others cleave double-stranded nucleic acid molecules. An oligo that forms a stem loop, and thereby provides a double-stranded region that can serve as a substrate for double-strand-specific nucleases. For instance, the following probe, in which a fluorophore is on the 5'-end and quenchers on the 3'-end, will form a double-stranded region with a SnaBI restriction enzyme recognition site. The double-stranded region can also serve as a substrate for sequence non-selective nucleases such as endonuclease I of *E. coli*.

```
                                              (SEQ ID NO: 4)
/5BiotinTEG//iCy3/ACTACGTAGTCACAACTACGTAGT/ZEN//
3IAbRQSp/
```

Note that the Cy3 fluorophore on this probe can be distinguished from the Cy5 fluorophore used in the Poly T probe of the Example. These two probes can thus be used in combination to detect distinct nucleases in a multiplexed format.

A self-hybridizing probe configuration can also be used to detect nucleases that digest double-stranded nucleic acid substrates. For instance, the following probe hybridizes with other copies of itself to form duplexes that yield quenched fluorescent double-stranded DNA probes:

```
5'-/56-FAM//CTACGTAG//ZEN/3IAbRQSp/-3'
```

This probe forms a substrate for the SnaBI restriction enzyme and is efficiently activated by sequence non-selective endonuclease I of *E. coli* (Flenker, K. S., Burghardt, E. L., Dutta, N., Burns, W. J., Grover, J. M., Kenkel, E. J., Weaver, T. M., Mills, J., Kim, H., Huang, L., et al. (2017). Rapid Detection of Urinary Tract Infections via Bacterial Nuclease Activity. Mol Ther 25, 1353-1362).

Fluorophores

In certain embodiments, the oligonucleotides of the present invention are operably linked to one or more fluorophores, which may also be called a "fluorescent tag." A fluorophore is a molecule that absorbs light (i.e. excites) at a characteristic wavelength and emits light (i.e. fluoresces) at a second lower-energy wavelength. Fluorescence reporter groups that can be incorporated into Substrate compositions include, but are not limited to, fluorescein, tetrachlorofluorescein, hexachlorofluorescein, tetramethylrhodamine, rhodamine, cyanine-derivative dyes, Texas Red, Bodipy, and Alexa dyes. Characteristic absorption and emission wavelengths for each of these are well known to those of skill in the art.

A fluorescence quencher is a molecule that absorbs or releases energy from an excited fluorophore (i.e., reporter), returning the fluorophore to a lower energy state without fluorescence emission at the wavelength characteristic of that fluorophore. For quenching to occur, reporter and quencher must be in physical proximity. When reporter and quencher are separated, energy absorbed by the reporter is no longer transferred to the quencher and is instead emitted as light at the wavelength characteristic of the reporter. Appearance of a fluorescent signal from the reporter group following removal of quenching is a detectable event and constitutes a "positive signal" in the assay of the present invention, and indicates the presence of nuclease in a sample.

Fluorescence quencher groups include molecules that do not emit any fluorescence signal ("dark quenchers") as well as molecules that are themselves fluorophores ("fluorescent quenchers"). Substrate compositions that employ a "fluorescent quencher" will emit light both in the intact and cleaved states. In the intact state, energy captured by the reporter is transferred to the quencher via FRET and is emitted as light at a wavelength characteristic for the fluorescent quencher. In the cleaved state, energy captured by the reporter is emitted as light at a wavelength characteristic for the reporter. When compositions that employ fluorescent quenchers are used in a FRET assay, detection must be done using a fluorometer. In certain embodiments, Substrate compositions that employ a "dark quencher" will emit light only in the cleaved state, enabling signal detection to be performed visually (detection may also be done using a fluorometer). Visual detection is rapid, convenient, and does not require the availability of any specialized equipment. It is desirable for an RNase detection assay to have visual detection method as an available option. Substrate compositions employing a "dark quencher" enable a visual detection endonuclease assay while Substrate compositions employing a "fluorescent quencher" are incompatible with a visual detection assay.

In one embodiment of the invention, the Substrate is comprised of a fluorescence quencher group that does not itself emit a fluorescence signal, i.e. is a "dark quencher". "Dark quenchers" useful in compositions of the invention include, but are not limited to, dabcyl, QSY™-7, QSY-33 (4',5-dinitrofluorescein, pipecolic acid amide) and Black-Hole Quenchers™ 1, 2, and 3 (Biosearch Technologies, Novato, Calif.). Assay results (i.e., signal from cleaved Substrate) can thus be detected optically. Optionally, the fluorescence signal can be detected using a fluorometer or any other device capable of detecting fluorescent light emission in a quantitative or qualitative fashion; for instance, fluorescence can be detected with a flow cytometer, a fluorescence microscope or a scanner.

In certain embodiments, the fluorophore is one or more of the fluorophores listed in Table 1.

TABLE 1

| Probe | Excitation (nm) | Emission (nm) |
| --- | --- | --- |
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |

TABLE 1-continued

| Probe | Excitation (nm) | Emission (nm) |
| --- | --- | --- |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |

In certain in vivo embodiments, the fluorophore emits in the near infrared range, such as in the 650-900 nm range. (Weissleder et al., "Shedding light onto live molecular targets, *Nature Medicine,* 9:123-128 (2003)).

Fluorescence Quencher Group

In certain embodiments, the oligonucleotides of the present invention are operably linked to one or more fluorescence quencher group or "quencher."

In certain embodiments, the quencher is one or more of the quenchers listed in Table 2.

TABLE 2

| Quencher | Absorption Maximum (nm) |
| --- | --- |
| DDQ-I | 430 |
| Dabcyl | 475 |
| Eclipse | 530 |
| Iowa Black FQ | 532 |
| BHQ-1 | 534 |
| QSY-7 | 571 |
| BHQ-2 | 580 |
| DDQ-II | 630 |
| Iowa Black RQ | 645 |
| QSY-21 | 660 |
| BHQ-3 | 670 |
| IRDye QC-1 | 737 |
| ZEN | 532 |

Additional quenchers are described in U.S. Pat. No. 7,439,341, which is incorporated by reference herein.

Linkers

In certain embodiments, the oligonucleotide is linked to the fluorophore and/or quencher by means of a linker.

In certain embodiments, an aliphatic or ethylene glycol linker (as are well known to those with skill in the art) is used. In certain embodiments, the linker is a phosphodiester linkage. In certain embodiments, the linker is a phosphorothioate or a phosphorodithioate linkage. In certain embodiments, other modified linkages between the modifier groups like dyes and quencher and the bases are used in order to make these linkages more stable, thereby limiting degradation to the nucleases.

In certain embodiments, the linker is a binding pair. In certain embodiments, the "binding pair" refers to two molecules that interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin.

In certain embodiments, the oligonucleotide is linked to the fluorophore and/or quencher by means of a covalent bond.

In certain embodiments, the oligonucleotide probe, i.e., an oligonucleotide that is operably linked to a fluorophore and quencher, is also operably linked to a solid substrate. For example, the oligonucleotide probe may be linked to a magnetic bead.

Chemistries that can be used to link the fluorophores and quencher to the oligonucleotide are known in the art, such as disulfide linkages, amino linkages, covalent linkages, etc. In certain embodiments, aliphatic or ethylene glycol linkers that are well known to those with skill in the art can be used. In certain embodiments, phosphodiester, phosphorothioate and/or other modified linkages between the modifier groups like dyes and quencher are used. These linkages provide stability to the probes, thereby limiting degradation to nucleobases. Additional linkages and modifications can be found on the world-wide-web at trilinkbiotech.com/products/oligo/oligo modifications.asp.

Substrate Synthesis

Synthesis of the nucleic acid Substrate of the invention can be performed using solid-phase phosphoramidite chemistry (U.S. Pat. No. 6,773,885) with automated synthesizers, although other methods of nucleic acid synthesis (e.g., the H-phosphonate method) may be used. Chemical synthesis of nucleic acids allows for the production of various forms of the nucleic acids with modified linkages, chimeric compositions, and nonstandard bases or modifying groups attached in chosen places throughout the nucleic acid's entire length.

In certain embodiments a support structure is bound independently to the quencher and also separately bound to the nucleotide sequence-fluorophore. Upon cleavage of the nucleotide sequence the fluorophore will be released and its proximity to the quencher will lengthen causing loss of quenching. Similarly, in certain embodiments, the opposite configuration is developed where the fluorophore is separately bound to the substrate and the nucleotide sequence-quencher is bound.

Detection Methods

In certain embodiments, the present invention provides methods for detecting nucleases in a sample in vitro. The method of the invention proceeds in the following steps: (a) contacting an aqueous test sample suspected of containing at least one nuclease with at least one detection composition comprising an aqueous solution and a substrate probe (an oligonucleotide linked to a fluorophore and a quencher) to form an aqueous reaction mixture, (b) emulsifying the aqueous mixture in oil to form femtoliter-scale or picoliter-scale droplets in an emulsion, (c) incubating the femtoliter-scale or picoliter-scale droplets in the emulsion in order for the nuclease, if present, to digest the substrate probes linked to the microbeads, (d) recovering the microbeads, and (e) detecting fluorescence emitting from the microbeads.

"Test sample" refers to any material being assayed for endonuclease (e.g., ribonuclease) activity and in certain embodiments, will be a liquid. Solids can be indirectly tested for nucleases by washing or immersion in solvent, e.g., water, followed by assay of the solvent.

For example, one can contact a sample with an oligonucleotide probe as described herein, and detect the presence of bacterial endonucleases using a florometer.

In certain embodiments, the probes of the present invention are also useful to detect bacterial contamination in settings such as research laboratories.

Incubation. The Assay Mix (e.g., the test sample plus Substrate) is incubated. Incubation time and condition can vary from a few minutes to 24 hours or longer depending upon the efficiency of the reaction and the sensitivity required. Incubation times of one hour or less are desirable. Nucleases are catalytic. Increasing incubation time should therefore increase sensitivity of the Assay, provided that background cleavage of the Substrate (hydrolysis) remains low. As is evident, assay background is stable over time and Assay sensitivity increases with time of incubation. Incubation temperature can generally vary from room temperature to 37° C., but may be adjusted to the temperature optimum of a specific nuclease (e.g., ribonuclease) suspected as being present as a contaminant.

Signal Detection. Fluorescence emission can be detected using a number of techniques (U.S. Pat. No. 6,773,885). In one method of detection, visual inspection is utilized. Visual detection is rapid, simple, and can be done without need of any specialized equipment. Alternatively, detection can be done using fluorometry or any other method that allows for qualitative or quantitative assessment of fluorescent emission.

Visual Detection Method. Following incubation, the picoliter droplets are exposed to UV light to provide excitation of the fluorescence reporter group. A reaction mixture in which the Substrate remains intact will not emit fluorescent signal and will visually appear clear or dark. Absence of fluorescence signal constitutes a negative assay result. A reaction mixture in which the probe has been cleaved will emit fluorescent signal and will visually appear bright. Presence of fluorescence signal constitutes a positive assay result, and indicates the presence of nuclease activity in the sample.

The reaction mixture will ideally constitute a relatively small volume, for example ~100 microliters of aqueous phase prior to emulsification, although greater or lesser volumes can be employed.

The various steps (mixing, incubating, detecting), can be performed in one tube. In one embodiment, the tube is a small, thin-walled, UV transparent microfuge tube, although tubes of other configuration may be used. A "short wave" UV light source emitting at or around 254 nm is used in one embodiment for fluorescence excitation. A "long wave" UV light source emitting at or around 300 nm can also be employed. A high intensity, short wave UV light source will provide for best sensitivity. UV light sources of this kind are commonly found in most molecular biology laboratories. Visual detection can be performed at the laboratory bench or in the field, however sensitivity will be improved if done in the dark.

Fluorometric Detection Method. Following incubation fluorescence emission can be detected using a fluorometer. Fluorometric detection equipment includes, but is not limited to, single sample cuvette devices and multiwell plate readers. As before, mixing, incubation, and detection can be performed in the same vessel. Use of a multiwell plate format allows for small sample volumes, such as 200 µl or less, and high-throughput robotic processing of many samples at once. This format is used in certain industrial QC settings. The method also provides for the Assay to be performed in RNase free cuvettes. As before, mixing, incubation, and detection can be performed in the same vessel. Use of fluorometric detection allows for highly sensitive and quantitative detection.

Kits

The present invention further features kits for detecting nuclease (e.g., endonuclease) activity comprising a picodroplets (aqueous solution and substrate probes) and instructions for use. Such kits may optionally contain one or more of a positive control nuclease (e.g., endonuclease), nuclease-free water, and a buffer. It is also provided that the kits may include nuclease-free laboratory plastic ware, for example, thin-walled, UV transparent microtubes for use with the visual detection method and/or multiwell plates for use with plate-fluorometer detection methods in a high-throughput format.

One kit of the invention includes a universal Substrate, the Substrate being sensitive to a broad spectrum of endonuclease (e.g., ribonuclease) activity. The kit is intended to detect endonuclease (e.g., ribonuclease) activity from a variety of sources. The assay is compatible with visual detection. In certain embodiments, the Substrate will be provided in dry form in individual thin-walled, UV transparent microtubes, or in multiwell (e.g., 96 well) formats suitable for high throughput procedures. Lyophilized Substrate has improved long-term stability compared to liquid solution in water or buffer. If provided in liquid solution, stability is improved with storage at least below −20° C., such as at −80° C. Storage in individual aliquots limits potential for contamination with environmental endonuclease (e.g., ribonucleases). Alternatively, the Substrate can be provided in bulk, either lyophilized or in liquid solution. Alternatively, substrate can be provided in bulk and can be dispersed at the discretion of the user.

An additional kit of the invention includes a set of enzyme-specific or enzyme-selective Substrates that together detect most RNase activities and individually can be used to distinguish between different endonuclease (e.g., ribonuclease) enzymes. Such a kit can be used to assess the nature and source of RNase contamination or can measure activity of specific enzyme of interest.

In Vitro Assays for Evaluating Nuclease Activity

In certain embodiments, the present invention provides in vitro assays for evaluating the activity of microbial nucleases on various nucleic acid substrates. In certain embodiments, the assay evaluates the activity of mycoplasma nucleases. In certain embodiments, the assay evaluates the activity of bacterial (e.g., *Staphylococcus aureus* or *Streptococcus pneumonia*) or viral nucleases. For example, a biological sample (e.g., tissue, cells, or biological fluids) or material derived from such a sample is combined with an oligonucleotide-based probe and incubated for a period to time. The fluorescence level of this reaction is then measured (e.g., with a fluorometer), and compared with the fluorescence levels of similar reactions that serve as positive and negative controls.

In certain embodiments, the present invention provides compositions and method for detecting the present and quantity of nucleases.

Detecting very low concentration of nucleases is quite challenging. Individual nuclease molecules have a limited capacity to digest substrates, and very dilute signals are difficult to detect (FIG. 1). In addition, nuclease reaction kinetics are non-linear, complicating efforts to quantify nuclease concentrations. The present invention addresses these problems by generating many parallel miniaturized reactions, which allows for much higher concentrations of digested substrates, and the output is digital (yes or no for activity) rather than continuous.

Figure 2:
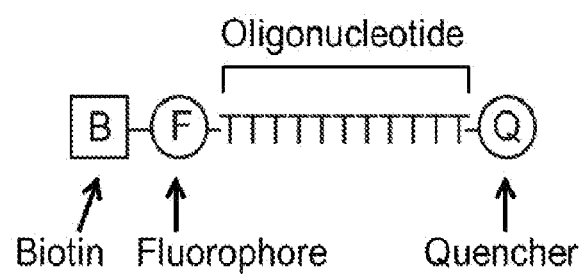
FIG. 2. An oligonucleotide probe for digital nuclease detection. Biotin enable coupling of the probe to streptavidin beads. Upon digestion of the oligonucleotide portion, the quencher diffuses away, resulting in fluorescent beads.
Figure 3:
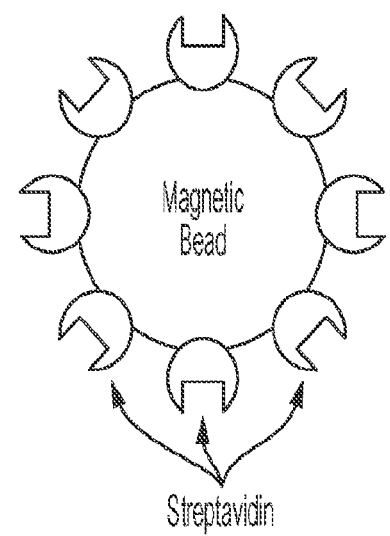
FIG. 3. Depiction of streptavidin-coupled magnetic beads. The capacity for certain beads are ~350,000 probe molecules per bead (MyOne Streptavidin C1 Dynabeads (Invitrogen)).
Figure 4:
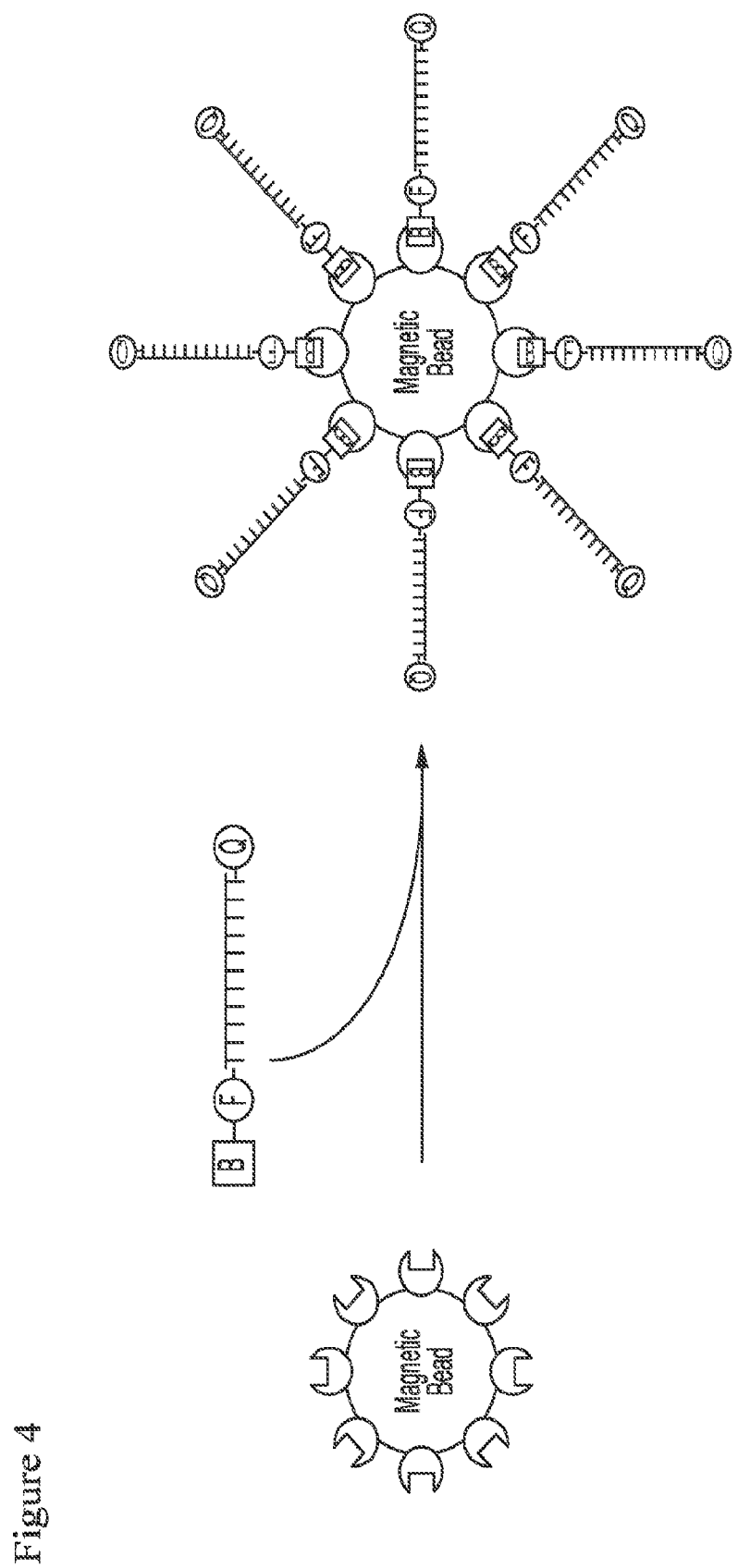
FIG. 4. Probe is coupled to beads via biotin-streptavidin interaction.
Figure 5:
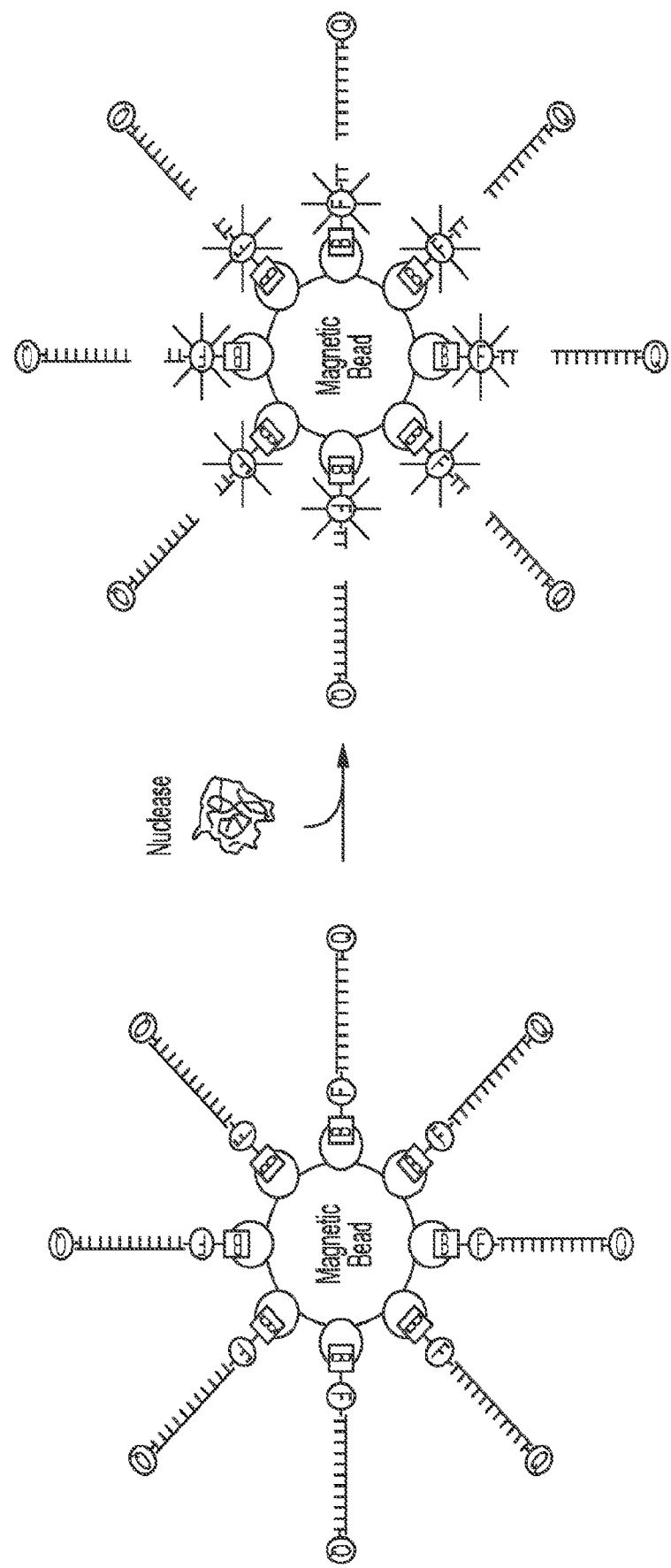
FIG. 5. Digestion of oligonucleotides releases quenchers from beads, resulting in large fluorescence increase (fluorophores remain bound to the beads).
Figure 6:
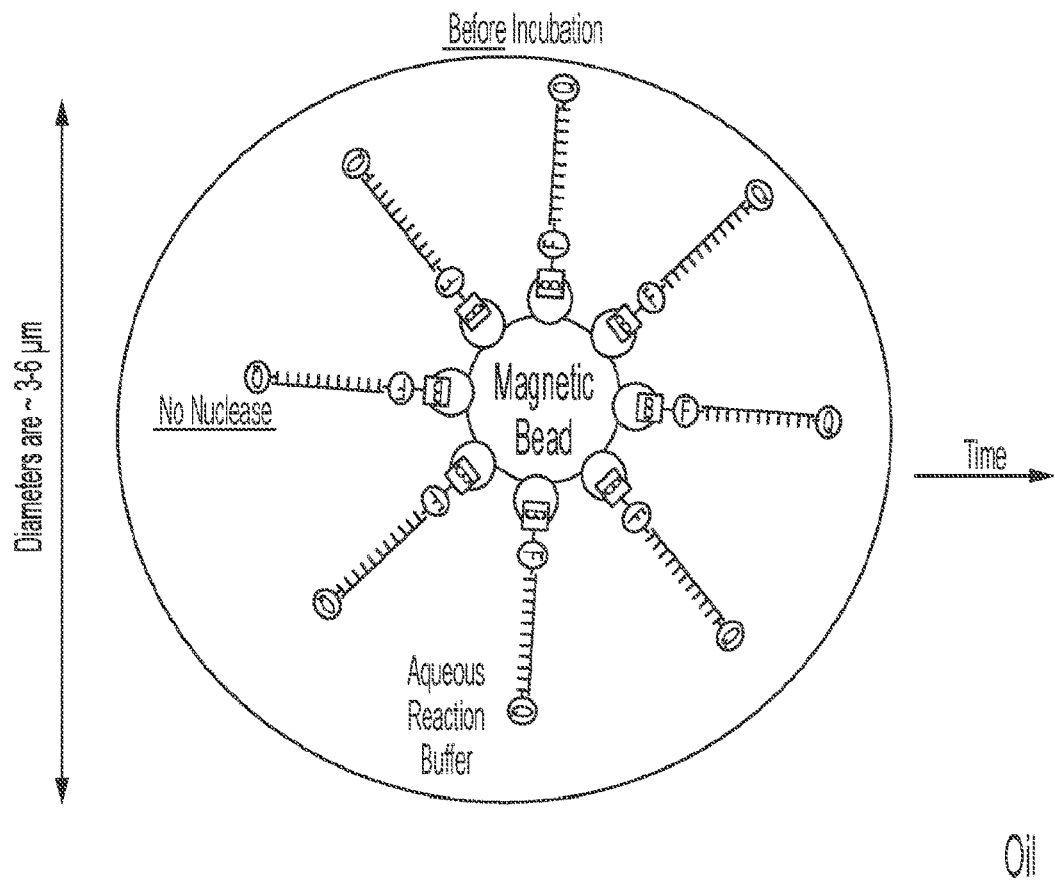
FIG. 6. Reaction compartmentalization via water-in-oil emulsion. Low concentrations of beads and nuclease will result in one or fewer beads per droplet and one or fewer nuclease molecules per droplet.
Figure 6:
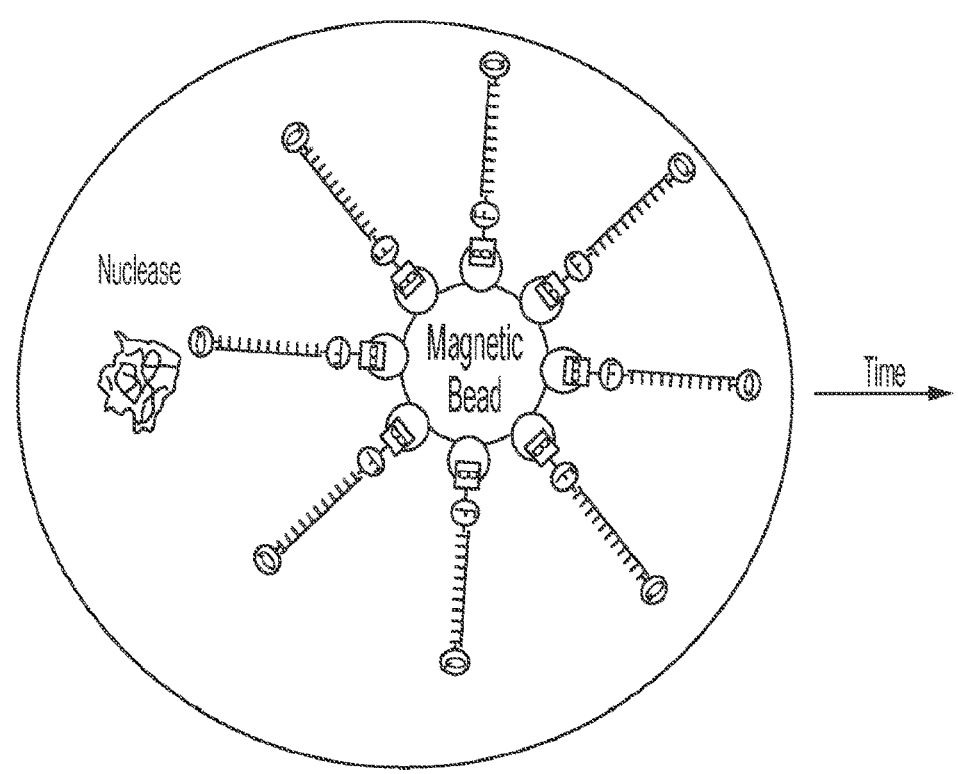
Figure 6:
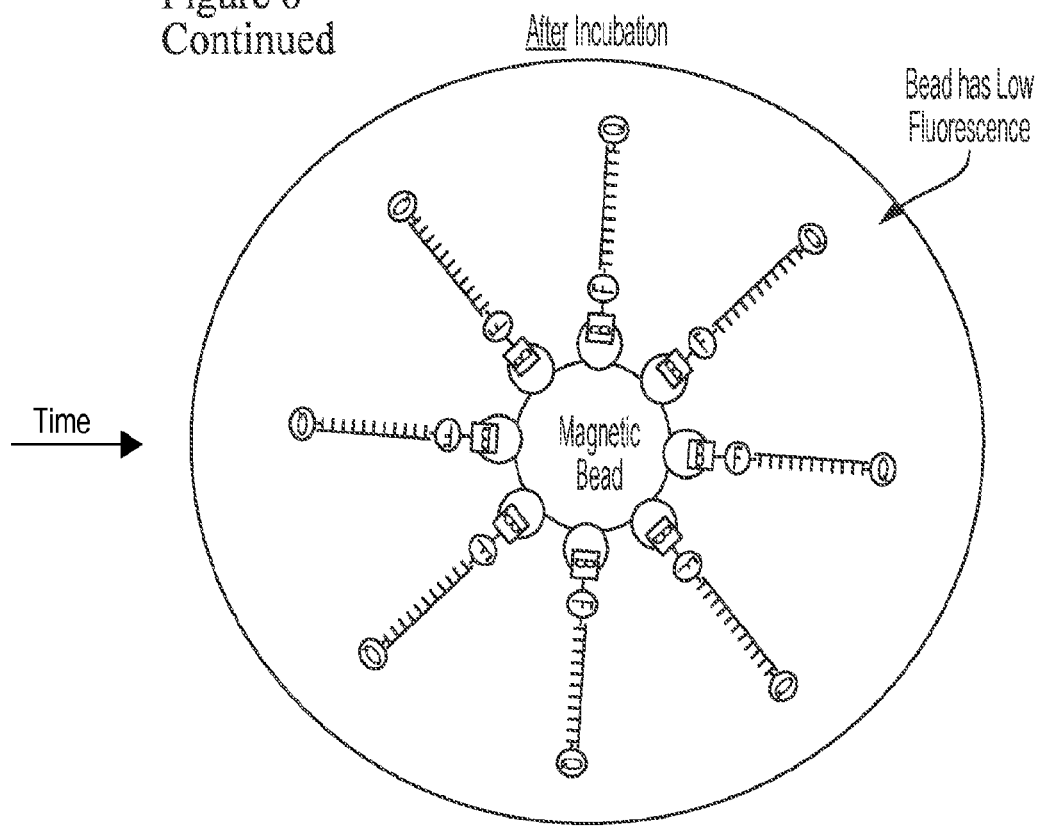
Figure 6:
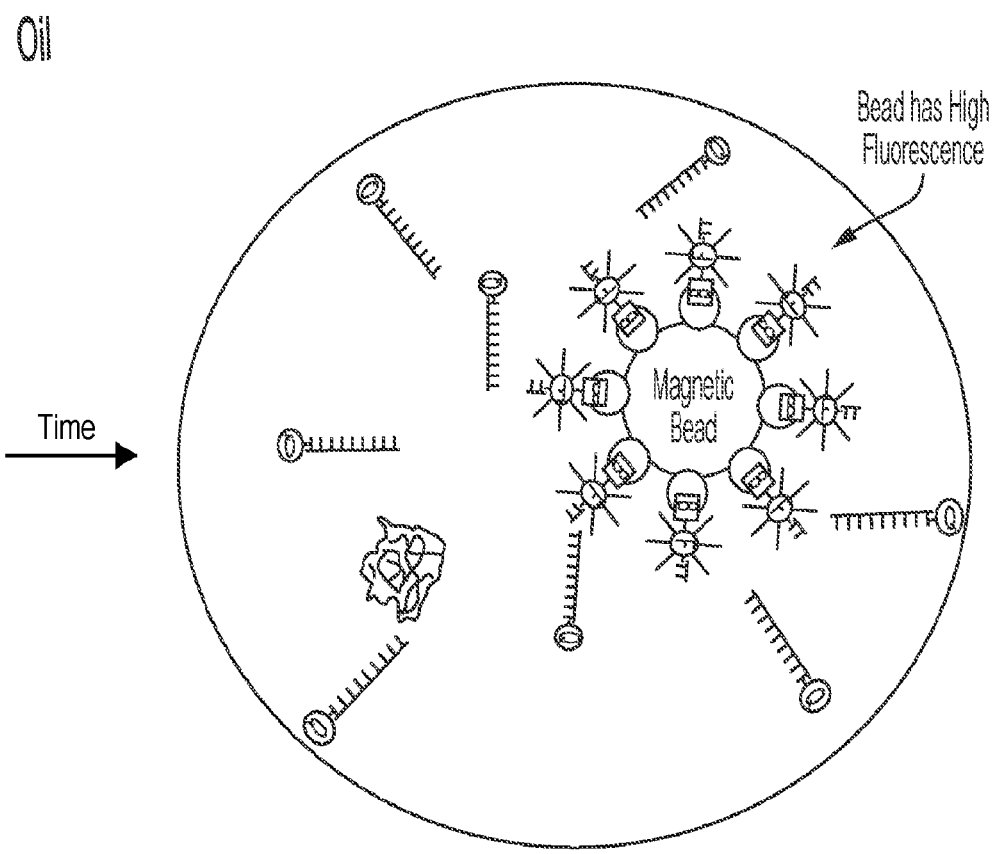

In certain embodiments, oligonucleotide probes are used for digital nuclease detection (FIG. 2). Biotin enables coupling of the probe to streptavidin beads. Upon digestion of the oligonucleotide portion, the quencher diffuses away, resulting in fluorescent beads. In certain embodiments, the probes are coupled to a magnetic bead, such as by means of a streptavidin-biotin interaction (FIGS. 3 and 4). The digestion of the oligonucleotides releases quenchers from beads, resulting in large fluorescence increase (fluorophores remain bound to the beads) (FIG. 5). In certain embodiments, the probe-coated beads are in an aqueous reaction buffer, and the buffer is emulsified in oil to produce "compartmentalized" picodroplets. Low concentrations of beads and nuclease will result in one or fewer beads per droplet and one or fewer nuclease molecules per droplet (FIG. 6).

Figure 7:
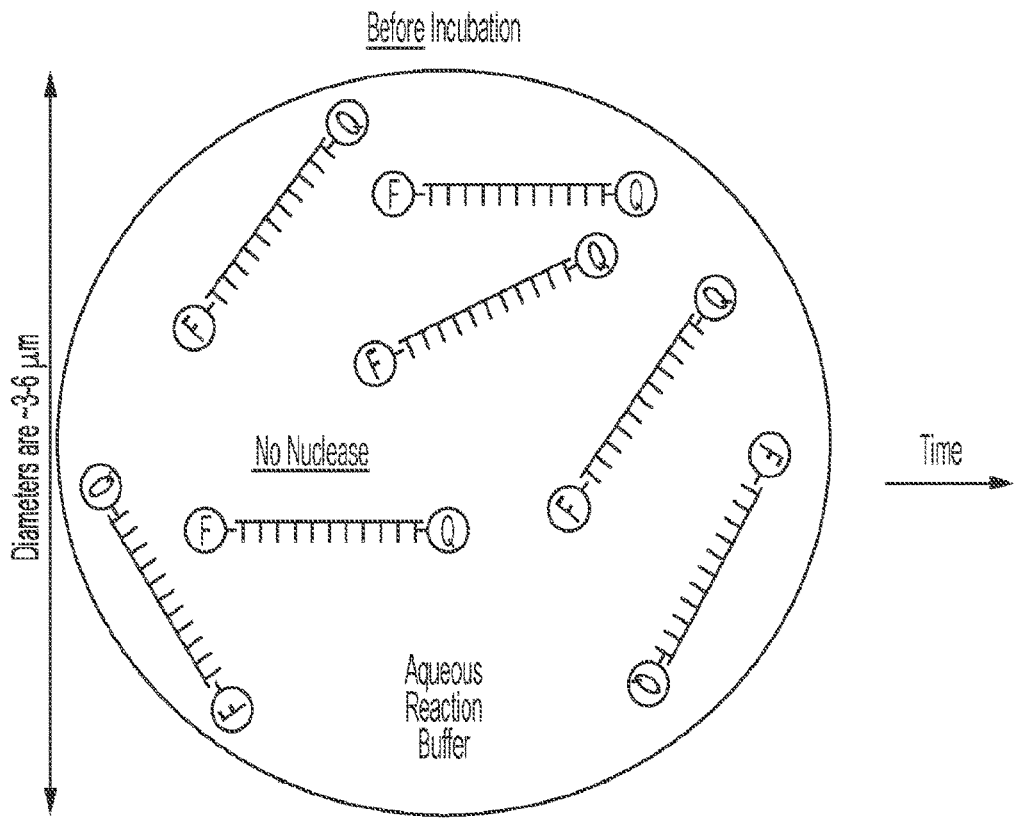
FIG. 7. A derivative of the probe-bead approach in which probes are in solution (i.e., no beads are present).
Figure 7:
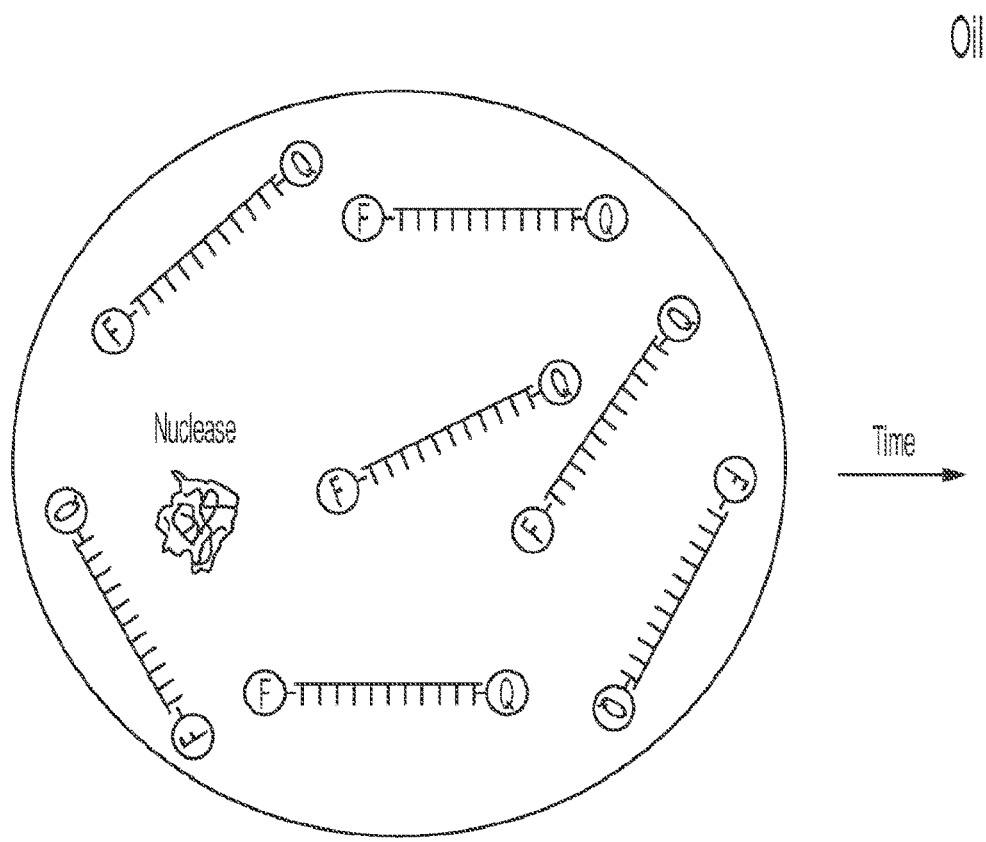
Figure 7:
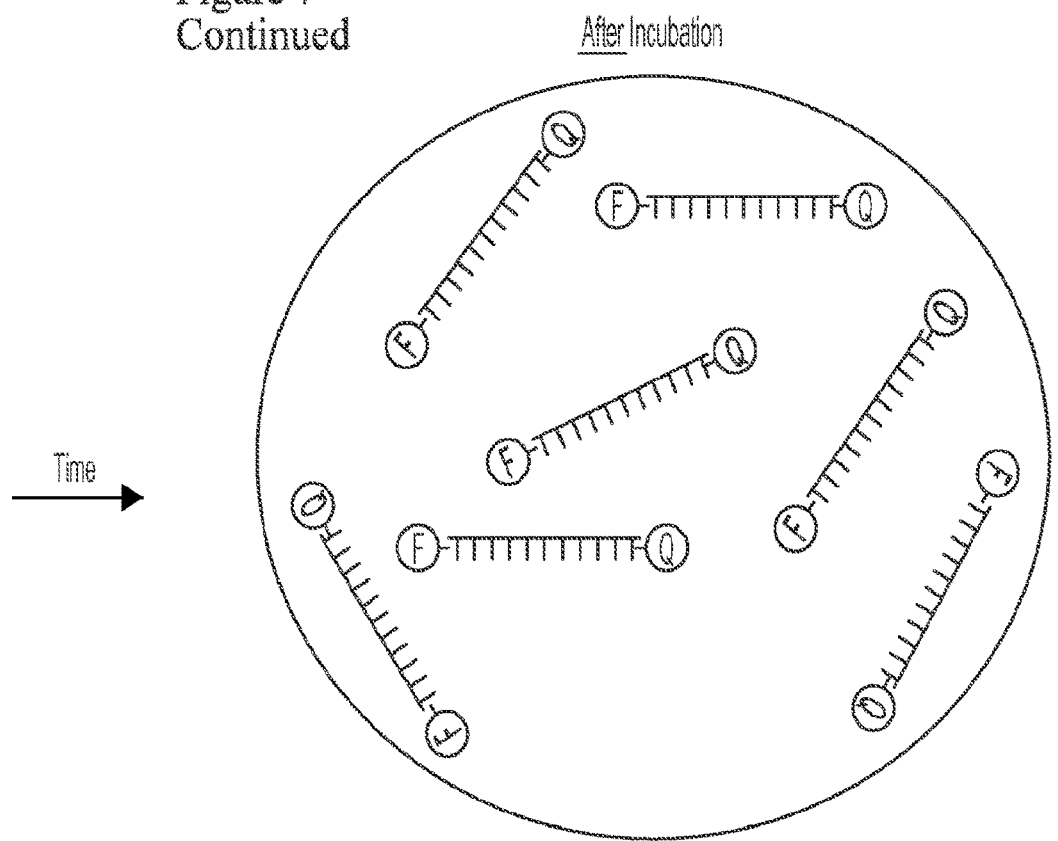
Figure 7:
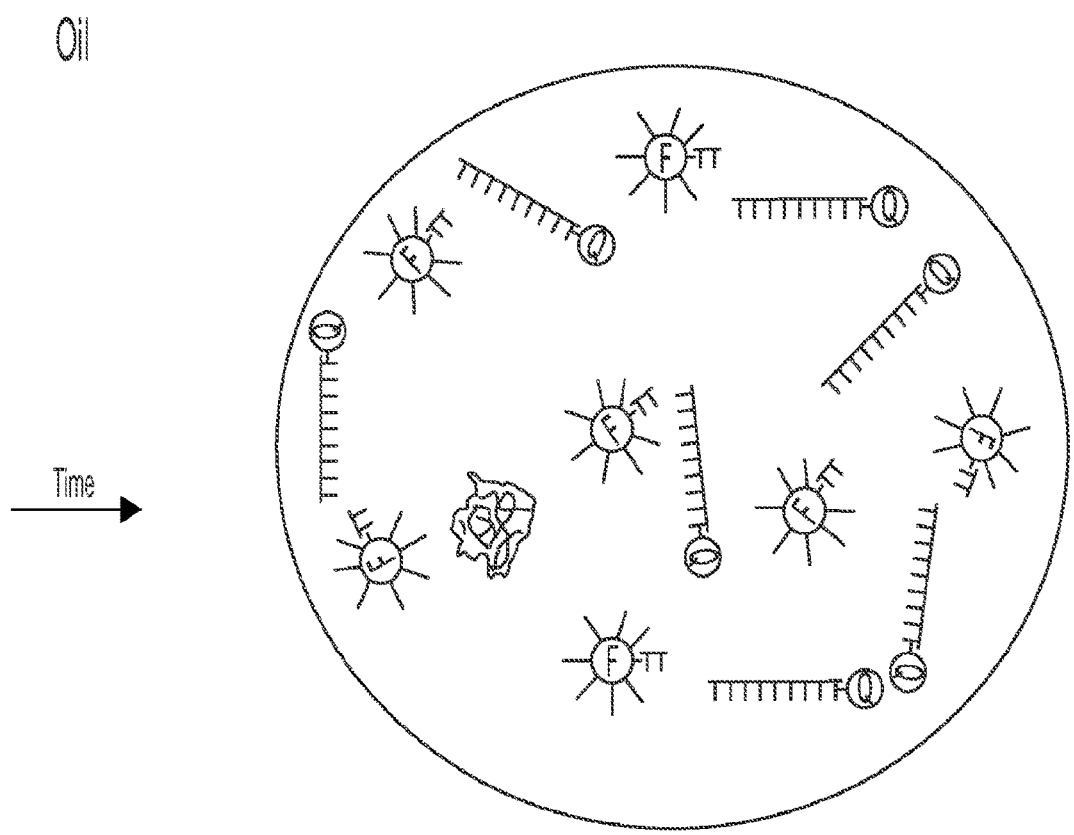

In certain embodiments, the probes are contained in picodroplets without the presence of microbeads. FIG. 7.

The invention is a method of detecting single target nuclease molecules in thousands of parallel, independent nanoliter or sub-nanoliter reactions. Fluorescence of each reaction indicates the presence of one (or more) or no nuclease molecules. Assuming random distribution, the nucleases will exhibit a Poisson distribution among the reactions. Total number of nucleases present in the initial solution are then be calculated. This method is used to precisely determine the number of nuclease molecules in a sample without a standard curve. The method has single molecule sensitivity at the level of the individual reactions.

Detection Compositions

In certain embodiments, the present invention provides a detection composition comprising a picodroplet comprising (a) an aqueous solution, and (b) a substrate probe comprising (i) an oligonucleotide of 2-75 nucleotides in length, (ii) a fluorophore operably linked to the oligonucleotide, and (iii) a quencher operably linked to the oligonucleotide. As used herein, the term "picodroplet" comprises a liquid droplet that has a volume of 0.014 to 2.6 picoliters.

In certain embodiments, the aqueous solution lacks magnesium.

In certain embodiments, the aqueous solution comprises a divalent cation chelator.

In certain embodiments, the aqueous solution comprises zinc or manganese.

In certain embodiments, the zinc or manganese is at a concentration of 100 µM to 20 mM.

In certain embodiments, the divalent cation chelator is EDTA.

In certain embodiments, the EDTA is at a concentration of 20-50 mM. In certain embodiments, the EDTA is at a concentration of 30 mM.

In certain embodiments, the oligonucleotide is 4-15 nucleotides in length.

In certain embodiments, the oligonucleotide is 4-11 nucleotides in length.

In certain embodiments, the oligonucleotide comprises one or more modified pyrimidines.

In certain embodiments, the oligonucleotide 15 TTTTTTTTTTT (SEQ ID NO:1).

In certain embodiments, the one or more of the nucleotides are chemically modified.

In certain embodiments, the one or more of the pyrimidines are chemically modified.

In certain embodiments, the one or more of the pyrimidines are 2'-O-methyl modified.

In certain embodiments, the one or more of the pyrimidines are 2'-fluoro modified.

In certain embodiments, the one or more of the purines, if present, are chemically modified.

In certain embodiments, the one or more of the purines are 2'-O-methyl modified.

In certain embodiments, the one or more of the purines are 2'-fluoro modified.

In certain embodiments, the fluorophore is selected from the group consisting of the fluorophores listed in Table 1.

In certain embodiments, the fluorophore has an emission in the near infrared range.

In certain embodiments, the quencher is selected from the group consisting of the quenchers listed in Table 2.

In certain embodiments, the oligonucleotide is single-stranded.

In certain embodiments, the oligonucleotide comprises both RNA and DNA.

In certain embodiments, the substrate probe is operably linked to a magnetic microbead. Magnetic microbeads are well-known in the art and are readily commercially available.

In certain embodiments, the microbead is about 0.5 to 20 µm in diameter.

In certain embodiments, the microbead is about 2 to 10 µm in diameter.

In certain embodiments, the microbead comprises a linking moiety.

In certain embodiments, the linking moiety is a streptavidin molecule. Others linking moieties include click chemistry linkers, amino linkers and thiol linkers. Exemplary linkers are well-known in the art (see, e.g., U.S. Patent Publication No. US-2010-0234450).

In certain embodiments, the substrate probe comprises a biotin moiety, and wherein the substrate probe is linked to the magnetic microbead through a biotin-streptavidin linkage.

In certain embodiments, the solution is a buffer with 0.1 to 20 mM $MgCl_2$ and 0.1 to 20 mM $CaCl_2$.

In certain embodiments, the solution is buffer with 0.1 to 20 mM $MgCl_2$, or $CaCl_2$ or other divalent cation.

In certain embodiments, the solution is buffer with no divalent cations and/or a chelator of divalent cations (EDTA).

In certain embodiments, the picodroplet is 0.014 to 2.6 picoliters.

In certain embodiments, the microbeads are present in a concentration that yields an average of less than one microbead per picodroplet.

Partitioning and Reaction Configurations

In one embodiment, the nuclease is captured with an affinity capture-based method, such as immunoprecipitation, on beads, such as magnetic beads (e.g., as in the example in (Burghardt, E. L., Flenker, K. S., Clark, K. C., Miguel, J., Ince, D., Winokur, P., Ford, B., and McNamara, J. O., 2nd (2016). Rapid, Culture-Free Detection of *Staphylococcus aureus* Bacteremia. PLoS One 11, e0157234), which are then partitioned into thousands or millions of small volume (femtoliter or picoliter scale) aqueous-phase reactions with a free (aqueous phase) oligonucleotide probe that can be digested (activated) by the nuclease. In this case, the concentration of the beads is such that 0 or 1 bead will be present per small volume reaction. The concentration of the nuclease is such that on average, 0 or 1 nuclease molecule will be present on each bead. This format was used to measure β-galactosidase immobilized on microscale beads which were then isolated in femtoliter-scale reactions that were partitioned on hydrophilic-in-hydrophobic surfaces (Kim, S. H., Iwai, S., Araki, S., Sakakihara, S., Iino, R., and Noji, H. (2012). Large-scale femtoliter droplet array for digital counting of single biomolecules. Lab Chip 12, 4986-4991).

In one embodiment, the probe is fixed to a solid surface, such as thousands or millions of spots or wells of micrometer-scale dimensions of a hydrophilic surface etched onto a hydrophobic surface. In other words, the probes would be located on discrete micrometer-scale spots or wells of hydrophilic surface, surrounded by hydrophobic surface that serves to isolate the hydrophilic spots or wells from one another. A sample consisting of a nuclease dissolved in a reaction buffer would then be applied to the surface and femtoliter or picoliter volume partitions of this sample would be isolated on each spot or well, yielding many distinct nuclease reactions. The concentration of the nuclease would be such that on average, 0, 1 or a small number of nuclease molecules would be present per partitioned femtoliter or picoliter reaction.

In one embodiment, the nuclease is free within an aqueous phase sample and is then combined with an aqueous phase solution comprising a quenched fluorescent oligonucleotide probe to create a reaction mixture. This mixture is then emulsified in oil to generate thousands or millions of small volume (femtoliter or picoliter scale) aqueous-phase droplets that serve as partitioned reactions. After an incubation period, the fluorescence levels of the droplets is measured with a suitable instrument, such as a fluorescence microscope.

Smaller Reaction Volume is Expected to Yield Nuclease Detection at Earlier Time-Points The rate of probe digestion in digital enzyme assays has been found to be inversely proportional to the volume of the reactions (Basu, A. S. (2017b). Digital Assays Part II: Digital Protein and Cell Assays. SLAS Technol 22, 387-405). In one embodiment, the volume of the partitioned reactions is less than 14 femtoliters, such as 1 femtoliter or 0.5 femtoliters.

The faster rate of probe digestion in smaller volumes is expected to enable detection of nuclease activity at earlier time points, such as minutes after reaction assembly. In one embodiment, the incubation time of the partitioned reactions is 30 seconds to 1 hour.

Possible Use of Reaction Kinetics to Distinguish Between Distinct Nucleases

The rate of probe digestion in digital enzyme assays has been found to be proportional to the enzyme turnover rate (i.e., the rate at which the enzyme digests probes) (Basu, A. S. (2017b). Digital Assays Part II: Digital Protein and Cell Assays. SLAS Technol 22, 387-405). The measurement of fluorescence of reactions at several time-points enables the measurement of the kinetics of the reactions. Because distinct nucleases (e.g., micrococcal nuclease versus snake venom phosphodiesterase) will exhibit different turnover rates for a particular substrate, reaction kinetic measurements can provide an indication of the identity of the nuclease in a reaction. In one embodiment, the reaction kinetics of thousands or millions of picoliter or femtoliter scale partitioned nuclease reactions are determined by measuring the fluorescence levels that indicate reaction progress (i.e., where fluorescence increase results from digestion of a quenched fluorescent oligonucleotide probe) at multiple time-points. The rates of fluorescence generation are then used to distinguish between distinct nucleases that may be present in the sample. The quantities of these nucleases and thus their concentration in the initial sample can also be determined from the fraction of reactions that have and/or do not have a particular nuclease whose kinetic signature is measured.

The reaction kinetic signatures of particular enzymes may also be distinguished with simpler, end-point fluorescence measurements; i.e., measurement of fluorescence at the conclusion of a single incubation period. In this case, the fluorescence level of some reactions that contain a nuclease may be higher than the basal level, while others that contain a distinct nuclease, in addition to being higher than the basal level, will also be higher than those that contain the first nuclease. In one embodiment, the reaction kinetics of thousands or millions of picoliter or femtoliter scale partitioned nuclease reactions are inferred by measuring the fluorescence levels that indicate reaction progress (i.e., where fluorescence increase results from digestion of a quenched fluorescent oligonucleotide probe) at a single time-point (end-point measurement). The kinetic signatures that are inferred are then used to distinguish between distinct nucleases that may be present in the sample. The quantities of these nucleases and thus their concentration in the initial sample can also be determined from the fraction of reactions that have and/or do not have the particular nuclease whose kinetic signature is measured.

Reaction Partitioning Approaches

Emulsion of aqueous phase enzymatic reactions in silicone oil that enabled measurement of individual enzyme molecules was demonstrated decades ago (Rotman, B. (1961). Measurement of activity of single molecules of beta-D-galactosidase. Proc Natl Acad Sci USA 47, 1981-1991). Emulsions can be produced with a variety of approaches including sonication, vibration and microfluidic devices (e.g., see reviews: Basu, A. S. (2017a). Digital Assays Part I: Partitioning Statistics and Digital PCR. SLAS Technol 22, 369-386; Basu, A. S. (2017b). Digital Assays Part II: Digital Protein and Cell Assays. SLAS Technol 22, 387-405). The use of flow focusing microchannel microfluidic devices (flow focusing junctions) can produce emulsions with droplets of uniform sizes (Anna, S. L., Bontoux, N., and Stone, H. A. (2003). Formation of dispersions using "flow focusing" in microchannels. Appl Phys Lett 82, 364-366); such emulsions enable greater precision for digital enzyme detection (see Arayanarakool, R., Shui, L., Kengen, S. W., van den Berg, A., and Eijkel, J. C. (2013). Single-enzyme analysis in a droplet-based micro- and nanofluidic system. Lab Chip 13, 1955-1962). Step emulsion droplet generators can also be used to more rapidly generate emulsions.

Surface-immobilized droplets that serve as femtoliter or picoliter-scale reactions is an alternative partitioning approach to that of emulsions. For instance, a clear elastomer surface onto which micrometer-scale wells are etched can serve as the surface (Rondelez, Y., Tresset, G., Tabata, K. V., Arata, H., Fujita, H., Takeuchi, S., and Noji, H. (2005). Microfabricated arrays of femtoliter chambers allow single molecule enzymology. Nat Biotechnol 23, 361-365). After applying the aqueous phase reaction solution to the surface, a coverslip is lowered onto it, thus isolating femtoliter to picoliter scale reactions from one another. Inclusion of an inert, blocking protein, such as bovine serum albumin, can improve detection by blocking reductions in enzyme activity that could otherwise occur due to enzyme adsorption to the solid surface.

Another example of surface immobilization of reactions is the use of hydrophobic surfaces (e.g., a hydrophobic polymer of carbon-fluorine (CYTOP)) onto which micrometer-scale spots of hydrophilic surface (e.g., $SiO_2$) are etched (Sakakihara, S., Araki, S., Iino, R., and Noji, H. (2010). A single-molecule enzymatic assay in a directly accessible femtoliter droplet array. Lab Chip 10, 3355-3362). Upon applying an aqueous solution to the surface and subsequent replacement of the solution with a hydrophobic solution (e.g., fluorocarbon oil, such as Fluorinert FC40), femtoliter to picoliter scale droplets of the aqueous phase remain bound to the hydrophilic portions of the surface (which are then surrounded by the fluorocarbon oil) and can thus serve as the partitioned reactions.

Methods and reagents used for partitioning the reactions into femtoliter or picoliter scale volumes include those mentioned above and other such methods and reagents as are known in the art, including those used for digital PCR and digital ELISA methods (see for reviews: Basu, A. S. (2017a). Digital Assays Part I: Partitioning Statistics and Digital PCR. SLAS Technol 22, 369-386; Basu, A. S. (2017b). Digital Assays Part II: Digital Protein and Cell Assays. SLAS Technol 22, 387-405). These methods include chamber-based partitioning approaches and water-in-oil emulsions. Emulsion oils that can be used include those mentioned above (silicone oil, fluorocarbon oil such as Fluorinert FC40). Inclusion of surfactants in the oil are known to reduce loss of reaction reagents that can otherwise result from adherence of the reactants to the droplet surface and/or diffusion into the oil phase (A mixture of Span 80, Tween 80 and mineral oil is one example of a surfactant/oil mixture that has Roach, L. S., Song, H., and Ismagilov, R. F. (2005). Controlling nonspecific protein adsorption in a plug-based microfluidic system by controlling interfacial chemistry using fluorous-phase surfactants. Anal Chem 77, 785-796) been shown to be effective in generating stable water-in-oil emulsions (Miller, O. J., Bernath, K., Agresti, J. J., Amitai, G., Kelly, B. T., Mastrobattista, E., Taly, V., Magdassi, S., Tawfik, D. S., and Griffiths, A. D. (2006). Directed evolution by in vitro compartmentalization. Nat Methods 3, 561-570).

Detection Methods for Picoliter and Femtoliter Scale Enzymatic Reactions

Detection methods include imaging fluorescence levels of reactions with fluorescence microscopes fitted with charge-coupled device (CCD) cameras, intensified charge-coupled device (ICCD) cameras, electron-multiplying charge-coupled device (EMCCD) cameras, complementary metal-oxide semiconductor (CMOS) cameras or photomultiplier tubes (PMTs). In the case of imaging fluorescence in aqueous droplets in oil (emulsions), the droplets can be imaged within microfluidic devices. Flow cytometers have been used to detect fluorescent signals immobilized on microscale beads for digital PCR (Dressman, D., Yan, H., Traverso, G., Kinzler, K. W., and Vogelstein, B. (2003). Transforming single DNA molecules into fluorescent magnetic particles for detection and enumeration of genetic variations. Proc Natl Acad Sci USA 100, 8817-8822). Laser-induced fluorescence (LIF) cytometry has also been used to detect fluorescence in the Bio-Rad and Raindance digital droplet PCR systems. Also, flow cytometers can be used to measure the fluorescence of any of the partitioned reaction configurations in which small volume droplets are used if the emulsions are generated as water-in-oil-in-water emulsions as described in (Miller, O. J., Bernath, K., Agresti, J. J., Amitai, G., Kelly, B. T., Mastrobattista, E., Taly, V., Magdassi, S., Tawfik, D. S., and Griffiths, A. D. (2006). Directed evolution by in vitro compartmentalization. Nat Methods 3, 561-570).

Additional Fluorophores, Quenchers and Linkers

Other fluorophores, quenchers and linkers, in addition to those listed in this document that may be used for probes of the present invention are described in the 11th Edition of the Molecular Probes Handbook-A Guide to Fluorescent Probes and Labeling Technologies, which can be found online at thermofisher.com/us/en/home/references/molecular-probes-the-handbook.html. Atto dyes (sold by Sigma Aldrich) are also suitable fluorophores (see sigmaaldrich.com/life-science/cell-biology/detection/learning-center/atto.html. Fluorescence quenchers such as Atto-Tec fluorescence quenchers are suitable quenchers. Other suitable fluorophores, quenchers and linking chemistries can be found in the product offerings of Trilink Biotechnologies (trilinkbiotech.com), ChemGenes (chemgenes.com), Glen Research (glenresearch.com/index.php), Sigma Aldrich (sigmaaldrich.com), Atto-Tec (atto-tec.com), Integrated DNA Technologies (IDT) (idtdna.com/site) and Ambion thermofisher.com/us/en/home/brands/Invitrogen/ambion).

Methods of Detection

In certain embodiments, the present method is used to determine if a patient has an infection with a specific microbe.

In certain embodiments, the present method is used to quantify the level of pathogens present, which is important for distinguishing background from clinically significant levels.

In certain embodiments, the present nuclease detection method is used for food safety and to detect bioterrorism.

In certain embodiments, the present invention provides a method of detecting at least one individual nuclease present in a sample, (a) contacting an aqueous sample suspected of containing at least one nuclease with at least one detection composition to form an aqueous reaction mixture, wherein the detection composition comprises a picodroplet comprising an aqueous solution and a substrate probe operably linked to a magnetic microbead, and wherein the substrate probe comprises (i) an oligonucleotide of 2-75 nucleotides in length, (ii) a fluorophore operably linked to the oligonucleotide, and (iii) a quencher operably linked to the oligonucleotide, (b) emulsifying the aqueous mixture in oil to form picoliter-scale droplets in an emulsion, (c) incubating the picoliter-scale droplets in the emulsion in order for the nuclease, if present, to digest the substrate probes linked to the microbeads, (d) recovering the microbeads, and (e) detecting fluorescence emitting from the microbeads.

In certain embodiments, the method further comprises (f) quantifying the fluorescence of the microbeads by flow cytometry.

In certain embodiments, the method further comprises (f) quantifying the fluorescence of the microbeads by microscopy.

In certain embodiments, the sample is blood, serum, plasma or a blood extract (e.g., one or more nucleases purified from blood), stool, sweat, skin extract, urine, synovial fluid, peritoneal fluid, cerebrospinal fluid, vitreous humor, lung lavage, or nasal extract, or material derived from any of these samples.

In certain embodiments, the sample is diluted sufficiently to yield some picodroplets with nuclease and some without nuclease.

In certain embodiments, the oil is a mixture of mineral oil, ABIL WE09 and Tegasoft DEC; or silicone oil; or a fluorocarbon oil such as Fluorinert FC40; or a mixture of Span 80, Tween 80 and mineral oil.

In certain embodiments, the incubating is for 2-10 hours.

In certain embodiments, the incubating is for 4-5 hours.

In certain embodiments, in step (a) the aqueous sample is contacted with two detection compositions, wherein each detection composition has a different florescent label.

In certain embodiments, the reaction mixture volume is less than a nanoliter.

The invention is now illustrated by the following non-limiting Examples.

EXAMPLE 1

Previous unpublished experiments used quenched fluorescent oligonucleotide probes to detect micrococcal nuclease of *S. aureus* indicated that as few as ~330 molecules of this nuclease could be detected in ~50 microliter reactions. These were based on methods described in Burghardt, E. L. et al. Rapid, Culture-Free Detection of *Staphylococcus aureus* Bacteremia. *PLoS One* 11, e0157234, doi:10.1371/journal.pone.0157234 (2016). This ultra-high sensitivity led the present investigators to consider whether such probes could enable the detection of single molecules of the nuclease. It was reasoned that methods that miniaturize the reaction volumes (e.g., to picoliter scales) could enable a substantial increase in detection sensitivity beyond what was observed with microliter scale reactions. With a quenched fluorescent oligonucleotide probe format, nuclease digestion of the probes is detected via the resulting release of unquenched fluorophores into the reactions. These fluorophores become diluted in larger volume reactions due to diffusion, which reduces the ability to detect them. In smaller reaction volumes, the activated probes remain concentrated because their diffusion is limited by the small reaction volume. Furthermore, immobilization of the probes on beads provides a convenient way of keeping the digested fluorophore concentrated, thus facilitating detection of probe activation.

If it were possible to detect individual nuclease molecules in small volume reactions, then it would be possible to quantify the number of nucleases present in a sample without a standard curve, because each reaction can be scored as positive or negative for nuclease. Whereas the progress of enzymatic reactions is generally non-linear, which complicates quantification of enzymes, an all-or-none accounting of nuclease presence in each reaction enables the simple calculation of the total number of nucleases present in the starting sample. The total number of nucleases present in positive reactions divided by the total volume of positive and negative reactions yields the nuclease concentration in the sample. For conditions in which multiple nucleases are present in some reactions (these may be indistinguishable from reactions with only a single nuclease), the total number of nucleases can be calculated from the fraction of reactions that is negative (see below for example). The random distribution of nucleases among the reactions is described by a Poisson distribution; the fraction of reactions with 1, 2, 3, etc. nuclease molecules each can be calculated once the fraction of negative reactions is measured, yielding an accounting of the total number of nucleases. This, together with the total volume, provides a measure of the nuclease concentration. This approach for nuclease quantification is built on concepts developed for digital PCR in which small volume PCR reactions are used to quantify the number of template DNA molecules present in a sample via all-or-none PCR amplification (Vogelstein, B. & Kinzler, K. W. Digital PCR. *Proc Natl Acad Sci USA* 96, 9236-9241 (1999)).

To explore the possibility that small reaction volumes might enhance sensitivity of nuclease detection with quenched fluorescent probes, a protocol developed for digital PCR (known as BEAMing) was adapted to detect micrococcal nuclease with a poly-deoxythymidine quenched fluorescent probe immobilized on magnetic beads (Diehl, F. et al. BEAMing: single-molecule PCR on microparticles in water-in-oil emulsions. Nat Methods 3, 551-559, doi: 10.1038/nmeth898 (2006); Dressman, D., Yan, H., Traverso, G., Kinzler, K. W. & Vogelstein, B. Transforming single DNA molecules into fluorescent magnetic particles for detection and enumeration of genetic variations. Proc Natl Acad Sci USA 100, 8817-8822, doi:10.1073/pnas.1133470100 (2003)). Digestion of the probe molecules on a bead results in unquenched fluorophores being left on the bead surface, which results in a fluorescent bead. (The probe-coupled beads of the present protocol replaced the PCR primer-coupled beads of the BEAMing digital PCR protocol.) The idea for this approach is that an aqueous suspension of these probe-coupled beads is mixed with an aqueous sample containing dilute concentrations of nuclease; this mixture is then emulsified in oil (conditions for this were developed and described in the BEAMing digital PCR protocol), producing millions of small volume (picoliter-scale) droplets. A subset of these droplets contain a bead; among the bead-containing droplets prepared with dilute nuclease samples, some droplets contain no nuclease molecules and others contain 1, 2, 3, etc. nuclease molecules. After the emulsion is incubated for some period of time to allow nuclease molecules present in the droplets to digest the probe molecules on the beads, the beads are recovered from the emulsion and their fluorescence is measured. If single molecule detection sensitivity is achieved, all beads that were in a droplet with one or more nuclease molecules will have an elevated fluorescence that can be distinguished from the beads that were in droplets with no nuclease molecules.

Figure 8:
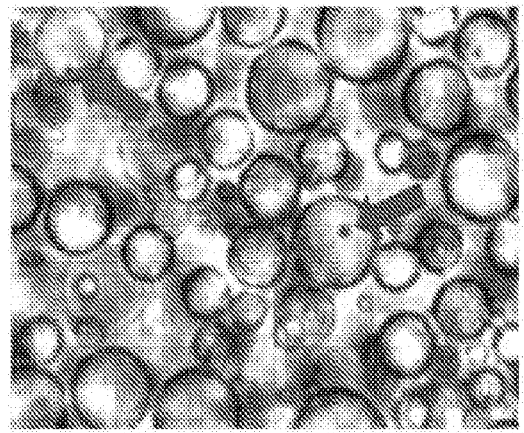
FIG. 8. Probe-coupled streptavidin beads (1 µm diameter; see arrows) isolated in water droplets in a water-in-oil emulsion.
Figure 9A:
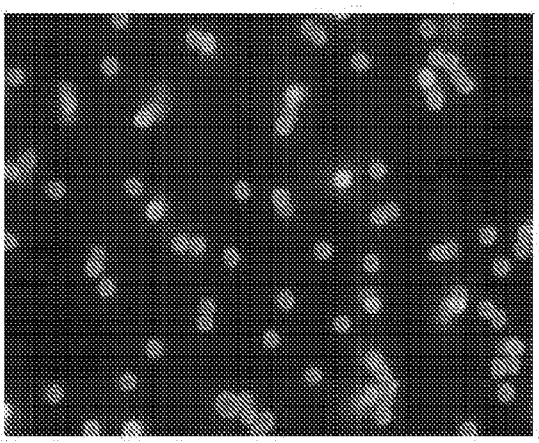
FIGS. 9A-9C. Florescence microscopy of beads coupled via biotin/streptavidin to a digital nuclease probe after incubation with buffer only (FIG. 9A), High concentration of micrococcal nuclease (~163 molecules of nuclease per 6 µm-diameter-droplet) (FIG. 9B) or a Low concentration of micrococcal nuclease (~0.2 molecules of nuclease per 6 µm-diameter-droplet) (FIG. 9C) of micrococcal nuclease in small volume droplets of aqueous buffer in oil. Note the presence of activated (solid arrows) and unactivated (hollow arrows) beads among the beads incubated with a low concentration of the nuclease.
Figure 9B:
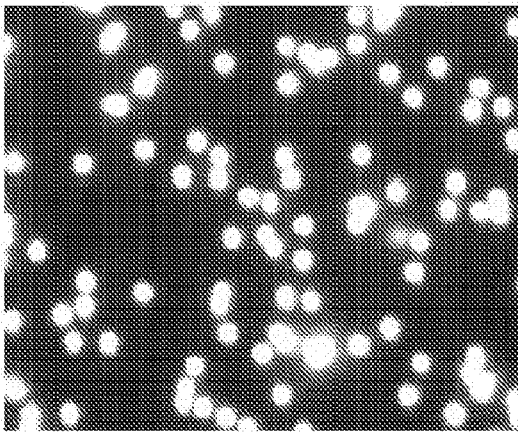
Figure 9C:
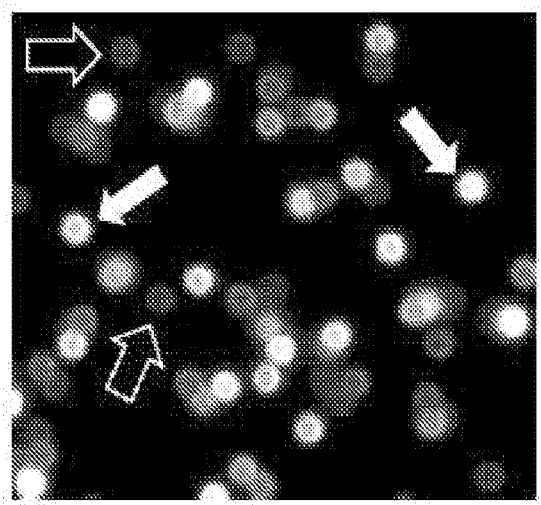
Figure 10:
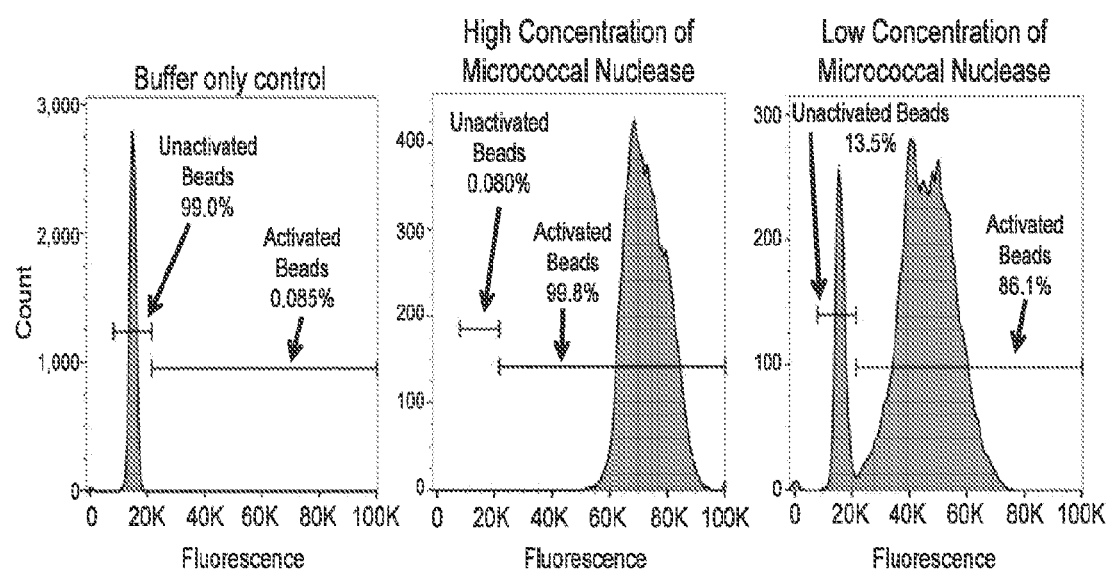
FIG. 10. Flow cytometry fluorescence measurements of beads coupled to a digital nuclease probe after incubation with buffer only (left), a high concentration (middle) or a low concentration (right) of micrococcal nuclease in small volume droplets of aqueous buffer in oil. Note the presence of activated and unactivated beads in the low nuclease concentration sample (right). Events were gated based on forward and side scatter to isolate single beads.

The following data support the concept of digital nuclease detection. A digital nuclease probe that is 5'-end labeled with biotin (FIG. 2) enables attachment of the probe to streptavidin-coated beads (~350,000 probe copies per 1 µm diameter bead). Nuclease digestion of the probe releases the quencher, resulting in fluorescent beads. By emulsifying aqueous suspensions of beads in oil, the beads are isolated in small droplets (FIG. 8). Including a very low concentration of nuclease in the aqueous suspension yields droplets that contain a bead and either 1) no nuclease molecules, or 2) one or more nuclease molecules. The ability to distinguish these two populations of reactions with fluorescence measurements enables digital molecular detection. In the experiment shown in FIGS. 9A-9C and 10, reactions included buffer only (left panels), a high concentration of MN (2.56 nM, middle panels) or a low concentration of MN (2.56 pM, right panels). As shown in FIGS. 9A-9C and 10 (see right panels), the populations of beads whose probes have been digested versus those that have not been digested can be clearly distinguished with fluorescence microscopy and flow cytometry, respectively. As with digital PCR, the concentration of target molecules in the sample can be calculated directly from the fraction of beads that are unactivated (see calculations below), given that the target molecules exhibit a Poisson distribution across the droplets (Vogelstein, B. & Kinzler, K. W. Digital PCR. *Proc Natl Acad Sci USA* 96, 9236-9241 (1999); Beer, N. R. et al. On-chip, real-time, single-copy polymerase chain reaction in picoliter droplets. *Anal Chem* 79, 8471-8475, doi:10.1021/ac701809w (2007)).

The low concentration of nuclease used (2.56 pM) was chosen for evaluation because this concentration results in substantial numbers of droplets with 0, 1 or a small number of nuclease molecules each. For instance, droplets with a diameter of 10 µm prepared with this concentration have an average number of nuclease molecules of 0.808 per droplet (whereas 808 molecules per droplet is the average for the higher nuclease concentration evaluated). For these conditions, based on a Poisson distribution of the nuclease molecules, 45% of droplets will have 0 nuclease molecules and 36% will have 1 nuclease molecule. The observed fraction of beads that was not activated in the sample with this low nuclease concentration was 13.5%, consistent with a droplet size that was slightly larger (~13.5 µm in diameter). Based on the range of droplet sizes in this sample (predominantly within 3-17 µm in diameter) and Poisson distribution modeling of MN within the droplets, these data are consistent with as few as one nuclease molecule yielding an activated bead if encapsulated in a droplet.

A random distribution of molecules among the droplets can be modeled with a Poisson distribution as follows: the probability of droplets having x number of MN molecules is $f(x)=(\mu^x e^{-\mu})/x!$, where µ is the mean number of MN molecules per droplet. For the case of 13.5% negative beads (see FIGS. 11 and 12), $f(0)=0.135=(\mu^0 e^{-\mu})/0!=(1 e^{-\mu})/1=e^{-\mu}$. Taking the natural logarithm of both sides of the equation, $\ln(0.135)=-2$ and $\ln(e^{-\mu})=-\mu$. µ, the mean number of MN molecules per droplet thus equals 2.

The fraction of droplets with 1 MN molecule each is calculated as shown in FIG. 12. These fractions (fractions with 0-8 nuclease molecules each) account for 99.976% of the droplets. Considering that droplets with more than eight nuclease molecules make up a negligible portion, it is possible to calculate the concentration of micrococcal nuclease in the sample as follows:

For 19,995 (0.99976×20,000) droplets total, the number of MN molecules in the reactions is:

$$
\begin{aligned}
&0 \times 0.135 \times 20{,}000\ + \\
&1 \times 0.270670566 \times 20{,}000\ + \\
&2 \times 0.270670566 \times 20{,}000\ + \\
&3 \times 0.180447044 \times 20{,}000\ + \\
&4 \times 0.090223522 \times 20{,}000\ + \\
&5 \times 0.036089409 \times 20{,}000\ + \\
&6 \times 0.012029803 \times 20{,}000\ + \\
&7 \times 0.003437087 \times 20{,}000\ + \\
&8 \times 0.000859272 \times 20{,}000\ = \\
&39{,}956\ \text{total } MN \text{ molecules}
\end{aligned}
$$

Using 13.5 µm for the droplet diameter (this is within the range of droplet diameters observed in the sample), the droplet volume=$(4/3)*\pi*(13.5\,\mu m/2)^3 = 1.29\times 10^{-15}\,m^3$. Converting this to liters by multiplying by 1,000 L/m$^3$ yields $1.29\times 10^{-12}$ L/droplet. The total volume in the droplets accounted for above is then 0.99976×20,000 droplets×$1.29\times 10^{-12}$ L=$25.8\times 10^{-9}$ L. The concentration is then (39,956 MN molecules)/(($25.8\times 10^{-9}$ L)×($6.02\times 10^{23}$ molecules/mole))= 2.57 pM.

The BEAMing protocol yields millions of picoliter-scale droplets, but the droplets are not a uniform size. Microfluidic methods have been developed to produce droplets of uniform sizes (Anna, S. L., Bontoux, N. & Stone, H. A. Formation of dispersions using "flow focusing" in microchannels. *Appl Phys Lett* 82, 364-366, doi:10.1063/1.1537519 (2003); Kiss, M. M. et al. High-Throughput Quantitative Polymerase Chain Reaction in Picoliter Droplets. *Analytical Chemistry* 80, 8975-8981, doi:10.1021/ac801276c (2008)). Use of these methods to generate droplets for nuclease detection simplifies the determination of the reaction volumes that are needed to calculate the nuclease concentrations from digital nuclease detection data as described above.

Materials and Methods

Oligonucleotide Probe

The PolyT Cy5 Btn oligonucleotide probe consisted of the following (written in IDT's nomenclature): 5'-/5Biotin-TEG//iCy5/TTTTTTTTTTT/ZEN//3IAbRQSp/-3', where 5BiotinTEG indicates a biotin moiety at the 5'-end followed by a linker, iCy5 indicates a Cy5 fluorophore, T indicates a deoxythymidine nucleotide, ZEN indicates IDT's ZEN quencher and 3IAbRQSp indicates the Iowa Black RQ quencher. Reference number of the batch of probe used is 154307304. The lyophilized probe was dissolved in TE (Invitrogen catalog #AM9849), for a final concentration of 100 µM.

Preparation of Probe-Coupled Magnetic Beads

The oligonucleotide probe was coupled to magnetic streptavidin-coupled beads (Dynabeads MyOne Streptavidin C1, Invitrogen catalog #65001). To couple the probe to the beads, 100 µl of beads were washed twice with 100 µl of Wash Buffer (20 mM Tris-HCl, pH 8.0, 50 mM NaCl), using a magnet to separate the beads from the aqueous phase each time. Then the beads were resuspended in a solution consisting of 10 µl of 100 µM PolyT Cy5 Btn probe combined with 100 µl Binding Buffer (5 mM Tris-HCl, pH 8.0, 0.5 mM EDTA, 1 M NaCl). This beads suspension was incubated at room temperature for 30 minutes; the suspension was mixed by gently pipetting up and down every 10 minutes. The liquid was then discarded and the beads were washed 3 times with Wash Buffer, resuspended in 100 µl Wash Buffer and stored at 4° C. until needed.

Preparation of Micrococcal Nuclease Stock

Purified micrococcal nuclease was obtained from Worthington (catalog number L5004797, Lot #R3P14588). 18,945 units of lyophilized nuclease (22,330 units/mg protein) was dissolved in 1.895 ml of 50% DPBS (no divalent cations), 50% glycerol and stored at −20° C. Total mass of protein in stock=18,945 units/22,330 units/mg=0.848 mg. Concentration of protein in stock=0.848 mg/1.895 ml=0.448 mg/ml=0.448 g/L. Molar concentration=0.448 g/L/16,900 g/mol=26.5 µM=26.5 µmol/µl. ($26.5\times 10^{12}$ moles/µl)×$6.02\times 10^{23}$ molecules/mole=$1.60\times 10^{13}$ molecules/µl.

Preparation of Emulsion Oil

Emulsion oil was prepared by combining 7% (by volume) ABIL WE-09 (Universal Preserv-A-Chem, Inc., item #100267-L151), 20% (by volume) Mineral Oil (Sigma catalog #M3516), 73% (by volume) Tegasoft DEC (Universal Preserv-A-Chem, Inc., item #270173-151), mixing gently and incubating at room temperature for at least 30 minutes.

Preparation and Execution of Reactions

Micrococcal nuclease was diluted from the stock solution into Reaction Buffer (50 mM Tris-HCl, pH 9.0, 10 mM CaCl$_2$) to yield dilutions of 1:10,000 (2.65 nM) and 1:10,000,000 (2.65 pM). 145 µl of each dilution, or Reaction Buffer only (negative control) was combined with 5 µl of probe-coupled magnetic beads. This yielded final concentrations of micrococcal nuclease in the aqueous phases of the reactions of 0, 2.56 nM and 2.56 pM. The concentration of beads in the reactions was ~$2.83\times 10^5$ beads/µl. Each of these mixtures was then immediately added to a 2 ml LoBind Eppendorf tube containing a 5 mm steel bead and 600 µl emulsion oil. The tubes were immediately placed in a cassette of a Qiagen TissueLyser II and shaken in the TissueLyser at 15 Hz for 10 seconds and then at 17 Hz for 7 seconds. This generated millions of reactions that consisted of aqueous phase droplets (some of which included a probe-coupled bead) suspended in the emulsion oil. Then 160 µl of each emulsion was transferred to each of 4 2-ml LoBind Eppendorf tubes and incubated at 37° C. for 5 hours. A portion of each emulsion that remained in the initial tube was streaked on a plastic tissue culture plate and imaged with a 40× objective in an Olympus IX71 inverted microscope fitted with a Hamamatsu cooled CCD camera, using brightfield to provide a rough measure of the droplet sizes.

Recovery of Beads from Emulsions

At the conclusion of the reaction time, 300 µl of Breaking Buffer (10 mM Tris-HCl, pH 8.0, 1% Triton X-100, 1 SDS, 100 mM NaCl, 1 mM EDTA) was added to each tube and tubes were immediately placed in a cassette of a Qiagen TissueLyser II and shaken in the TissueLyser at 20 Hz for 30 seconds. The tubes were then centrifuged at 3,200× G for 2 minutes. The oil layer of each was removed with a pipette tip connected to a vacuum line. 300 µl of additional Breaking Buffer was added to each and tubes were centrifuged again at 3,200× G for 2 minutes. Tubes were then placed on the magnet and liquid was drawn off and discarded. Beads from each corresponding set of 4 tubes (those that belonged to a particular reaction) were combined by suspending them in 100 µl of Wash Buffer. Each sample was then placed on the magnet again, liquid was discarded and beads were resuspended in a fresh 100 µl of Wash Buffer. Beads were then imaged with an inverted microscope and evaluated with flow cytometry or stored at 4° C. for analysis at a later time.

Imaging of Reacted Beads

10 µl of each recovered beads sample was pipetted onto the glass surface of a Mattek imaging dish (catalog #P35G-1.5-20-C) and imaged with an Olympus IX71 inverted fluorescence microscope equipped with fluorescence filters for Cy5, a cooled CCD camera (Hamamatsu), and a 40× oil immersion objective. Several brightfield and Cy5 fluorescence images were acquired for each sample after the beads had settled on the glass coverslip.

Flow Cytometry of Reacted Beads

The fluorescence of each beads sample was measured with flow cytometry. A Becton Dickinson LSR II flow cytometer was used to measure fluorescence of 10,000 to 20,000 beads whose forward and side scatter profiles indicated that they were present as single beads (not multiple or clumped beads). The fluorescence in the Cy5 channel was recorded for these beads.

EXAMPLE 2

In this Example, probe-coupled beads, emulsion mixture and instrument (a Qiagen TissueLyser II) to generate the emulsions were used. The beads were MyOne Streptavidin C1 Dynabeads. These were coupled to the probe described above. The emulsion oil was a mixture of three emulsion oils. These were combined as follows: 7% ABIL WE09, 20% Mineral oil, 73% Tegasoft DEC. The enzyme (micrococcal nuclease of *Staphylococcus aureus*) was purchased from Worthington and was diluted in 50 mM Tris-HCl, pH 9.0, 10 mM $CaCl_2$. For each reaction, 145 microliters of each enzyme dilution was combined with 5 microliters of probe-coupled beads (which were suspended in 20 mM Tris-HCl, pH 8.0, 50 mM NaCl) and then combined with 600 microliters of emulsion oil mixture and a 5 mm steel bead. These mixtures were shaken with a TissueLyser II as described in Diehl, F. et al. BEAMing: single-molecule PCR on microparticles in water-in-oil emulsions. Nat Methods 3, 551-559, doi:10.1038/nmeth898 (2006). A portion of each reaction was streaked on a tissue culture dish at this point and imaged with brightfield microscopy to verify that emulsions were formed. Then reactions were incubated at 37° C. for 5 hours before the emulsions were broken and beads were recovered as described in the paper. The beads were then imaged with fluorescence microscopy using filters appropriate for Cy5. The fluorescence of the beads was quantified with a flow cytometer (LSR violet).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A picodroplet composition having one and only one enzymatically active nuclease molecule, the picodroplet comprising
   (a) an aqueous solution lacking magnesium and/or comprising a divalent cation chelator, and
   (b) a substrate probe comprising
      (i) an oligonucleotide of 2 to 75 nucleotides in length,
      (ii) a fluorophore operably linked to the oligonucleotide, and
      (iii) a quencher operably linked to the oligonucleotide.

2. The picodroplet detection composition of claim 1, wherein the oligonucleotide is TTTTTTTTTT (SEQ ID NO:1).

3. The picodroplet composition of claim 1, wherein the solution is a buffer comprising 0.1 to 20 mM MgCl$_2$ and 0.1 to 20 mM CaCl$_2$, a buffer comprising 0.1 to 20 mM MgCl$_2$, a buffer comprising 0.1 to 20 mM CaCl$_2$, or a buffer comprising 0.1 to 20 mM of another divalent cation.

4. The picodroplet composition of claim 1, wherein the aqueous solution comprises zinc, manganese and/or calcium.

5. The picodroplet composition of claim 1, wherein the divalent cation chelator is EDTA.

6. The picodroplet composition of claim 1, wherein the oligonucleotide is 4 to 15 nucleotides in length.

7. The picodroplet composition of claim 1, wherein one or more of the pyrimidines, if present, are chemically modified.

8. The picodroplet composition of claim 7, wherein one or more of the pyrimidines are 2'-O-methyl modified and/or wherein one or more of the pyrimidines are 2'-fluoro modified.

9. The picodroplet composition of claim 1, wherein one or more of the purines, if present, are chemically modified.

10. The detection composition of claim 9, wherein one or more of the purines are 2'-O-methyl modified and/or wherein one or more of the purines are 2'-fluoro modified.

11. The detection composition of claim 1, wherein the oligonucleotide is single-stranded.

12. The detection composition of claim 1, wherein the oligonucleotide comprises DNA.

13. The detection composition of claim 1, wherein the substrate probe is operably linked to a magnetic microbead.

14. The detection composition of claim 13, wherein the microbead is about 0.5 to 20 μm in diameter.

15. The detection composition of claim 13, wherein the microbead comprises a linking moiety.

16. The detection composition of claim 13, wherein the substrate probe comprises a biotin moiety and wherein the substrate probe is linked to the magnetic microbead through a biotin-streptavidin linkage.

17. The detection composition of claim 13, wherein the microbeads are present in a concentration that yields an average of less than one microbead per picodroplet.

18. The detection composition of claim 17, wherein the picodroplet is 0.014 to 2.6 picoliters.

19. The detection composition of claim 1, wherein the pH of the detection composition is between 8.5 and 10.5, inclusive.

* * * * *

UNITED STATES PATENT AND TRADEMARK OFFICE
CERTIFICATE OF CORRECTION

PATENT NO. : 12,378,591 B2
APPLICATION NO. : 16/651863
DATED : August 5, 2025
INVENTOR(S) : James O. McNamara It is certified that error appears in the above-identified patent and that said Letters Patent is hereby corrected as shown below:

In the Claims

Column 30, Line 54, Claim 10, please delete "detection composition" and insert -- picodroplet composition --;

Column 30, Line 57, Claim 11, please delete "detection composition" and insert -- picodroplet composition --;

Column 30, Line 59, Claim 12, please delete "detection composition" and insert -- picodroplet composition --;

Column 30, Line 61, Claim 13, please delete "detection composition" and insert -- picodroplet composition --;

Column 30, Line 63, Claim 14, please delete "detection composition" and insert -- picodroplet composition --;

Column 30, Line 65, Claim 15, please delete "detection composition" and insert -- picodroplet composition --;

Column 31, Line 1, Claim 16, please delete "detection composition" and insert -- picodroplet composition --;

Column 31, Line 5, Claim 17, please delete "detection composition" and insert -- picodroplet composition --;

Column 31, Line 8, Claim 18, please delete "detection composition" and insert -- picodroplet composition --; and Signed and Sealed this
Tenth Day of February, 2026

John A. Squires
*Director of the United States Patent and Trademark Office*

CERTIFICATE OF CORRECTION (continued)
U.S. Pat. No. 12,378,591 B2

Column 31, Line 10, Claim 19, please delete "detection composition" and insert -- picodroplet composition -- therefor.